United States Patent
Wand et al.

(10) Patent No.: US 6,783,812 B2
(45) Date of Patent: Aug. 31, 2004

(54) ALKYL SILANE LIQUID CRYSTAL COMPOUNDS

(75) Inventors: Michael Wand, Boulder, CO (US); Neil Gough, Longmont, CO (US); Kundalika More, Denver, CO (US); William N. Thurmes, Longmont, CO (US); Xin-Hua Chen, Erie, CO (US)

(73) Assignee: Displaytech, Inc., Longmont, CO (US)

( * ) Notice: Subject to any disclaimer, the term of this patent is extended or adjusted under 35 U.S.C. 154(b) by 0 days.

(21) Appl. No.: 09/754,033

(22) Filed: Jan. 3, 2001

(65) Prior Publication Data

US 2002/0130299 A1 Sep. 19, 2002

Related U.S. Application Data

(60) Provisional application No. 60/256,063, filed on Dec. 15, 2000.

(51) Int. Cl.$^7$ .................. C09K 19/34; C09K 19/32; C09K 19/12; C07D 239/02; C07F 7/08
(52) U.S. Cl. .............. 428/1.1; 252/299.61; 252/299.62; 252/299.63; 252/299.64; 252/299.66; 544/303; 546/14; 570/129; 570/162; 556/488; 556/489
(58) Field of Search .............. 252/299.61, 299.62, 252/299.63, 299.64, 299.66; 544/303; 546/14; 556/488, 489; 570/129, 162; 428/1.1

(56) References Cited

U.S. PATENT DOCUMENTS

| | | | |
|---|---|---|---|
| 5,051,506 A | 9/1991 | Wand et al. | 544/289 |
| 5,061,814 A | 10/1991 | Wand et al. | 549/560 |
| 5,130,048 A | 7/1992 | Wand et al. | 252/299 |
| 5,167,855 A | 12/1992 | Wand et al. | 252/299.01 |
| 5,168,381 A | 12/1992 | Walba | 359/53 |
| 5,178,791 A | 1/1993 | Wand et al. | 252/299.6 |
| 5,178,793 A | 1/1993 | Vohra et al. | 252/299.61 |
| 5,180,520 A | 1/1993 | Wand et al. | 252/299.61 |
| 5,271,864 A | 12/1993 | Wand et al. | 252/299.61 |
| 5,278,680 A | 1/1994 | Karawawa | 359/40 |
| 5,380,460 A | 1/1995 | Wand et al. | 252/299.6 |
| 5,422,037 A | 6/1995 | Wand et al. | 252/299.61 |
| 5,453,218 A | 9/1995 | Wand et al. | 252/299.01 |
| 5,457,235 A | 10/1995 | Wand et al. | 568/65 |
| 5,539,555 A | 7/1996 | Wand et al. | 359/100 |
| 5,543,078 A | 8/1996 | Walba et al. | 252/299.65 |
| 5,585,036 A | 12/1996 | Wand et al. | 252/299.01 |
| 5,596,434 A | 1/1997 | Walba et al. | 349/123 |
| 5,626,792 A | 5/1997 | Wand et al. | 252/299.01 |
| 5,637,256 A | 6/1997 | Walba et al. | 252/299.66 |
| 5,658,493 A | 8/1997 | Walba et al. | 252/299.01 |
| 5,753,139 A | 5/1998 | Wand et al. | 252/299.01 |
| 5,866,036 A | 2/1999 | Wand et al. | 252/299.6 |

FOREIGN PATENT DOCUMENTS

DE   4427199   *  2/1996

OTHER PUBLICATIONS

CAPLUS 1995: 886137.*
CAPLUS 1996: 239763.*
English abstract of DE–4427199, 1996.*
Inui, S. et al. (1996) J. Mater. Chem. 8(4):671–673.
Seomun, S.S. et al. (1997) Jpn. J. Appl. Phys. 36:3580–3590.

* cited by examiner

Primary Examiner—Shean C. Wu
(74) Attorney, Agent, or Firm—Greenlee, Winner and Sullivan, P.C.

(57) ABSTRACT

Compounds useful as components of LC and FLC compositions which in turn are useful in the manufacture of optical devices. Compounds of this invention have a silane tail, which can contain more than one Si. Compounds of this invention can include those with disilane tails. The invention provides LC compositions containing one or more of the silanes of this invention. Addition of one or more of the compounds of this invention to LC compositions can result in significant improvement in optical or LC properties. In particular, the compounds of this invention can significantly lower the melting point, freezing point or both of an LC composition resulting in significant improvement in device stability.

41 Claims, No Drawings

ALKYL SILANE LIQUID CRYSTAL COMPOUNDS

CROSS-REFERENCE TO RELATED APPLICATIONS

This application takes priority under 119(e) from U.S. provisional application serial No. (60/256,063) filed Dec. 15, 2000. This provisional application is incorporated by reference in its entirety herein to the extent that it is not inconsistent with the disclosure herein.

BACKGROUND OF THE INVENTION

The present invention relates to compounds useful as components in liquid crystal (LC) compositions, particularly as components of LC compositions that exhibit smectic phases and more particularly as components of LC compositions that exhibit smectic A and/or smectic C phases. LC compositions of this invention may also exhibit nematic phases. LC compositions of this invention can be ferroelectric liquid crystals (FLCs). The invention also relates to optical devices employing LC compositions of the invention in optical switching and display elements.

Several types of smectic liquid crystal materials (LCs) have been investigated for rapid switching, view-angle enhancement and higher contrast, including surface-stabilized ferroelectric LCs (FLCs), deformed helix ferroelectric LCs (DHFLCs), and antiferroelectric LCs (AFLCs). Recently, smectic material exhibiting thresholdless or more properly V-shaped switching LCs (VSLCs) have been described (Inui, S. et al. (1996) J. Mater. Chem. 6(4):671–673; Seomun, S. S. et al. (1997) Jpn. J. Appl. Phys. 36:3580–3590). Ferroelectric LCs when aligned parallel to the substrate surfaces using the surface stabilized effect (in an surface-stabilized ferroelectric liquid crystal (SSFLC) device) exhibit two stable state switching on a microsecond time scale. Antiferroelectric LCs exhibit three stable-state switching, which by application of a bias field can be converted for use in a bistable switching mode LC devices. Two of the AFLC states have the same transmittance, so that alternate symmetrical switching can be used in AFLC devices. VSLCs, in contrast, exhibit very rapid, analog electro-optic response, allow symmetrical driving, and no dc balance is required. VSLCs are particularly attractive for applications requiring generation of multiple levels of gray scale.

Liquid crystal (LC) compositions exhibit one or more LC phases. LC compositions may be composed of one or more components. Components of LC compositions may exhibit liquid crystal phases, have latent liquid crystal phases or be compatible with (not suppress) liquid crystal phases in the LC composition. LC compounds and components of LC mixtures of this invention are rod-like molecules most typically having a generally linear mesogenic core with one or more directly or indirectly linked alicylic or aromatic rings (which may be fused aromatic rings) and linear or branched tail groups distributed on either side of the mesogenic core, e.g.:

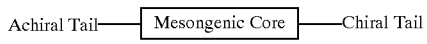

LC components which do not themselves exhibit liquid crystal phases, but which exhibit LC phases on combination with one or more other components are described as having "latent" liquid crystal phases. Chiral nonracemic LCs useful in FLCS, DHFLCS, AFLC and VSLCS compositions have at least one component that has a chiral non-racemic tail group. FLCS, DHFLCS, AFLC and VSLCS compositions may be composed entirely of chiral non-racemic components, but are typically composed of a mixture of chiral nonracemic and achiral or racemic components.

SUMMARY OF THE INVENTION

The invention relates to liquid crystal compounds having silane tails which are useful as components in liquid crystal compositions, particularly those compositions exhibiting smectic liquid crystal compositions and more particularly those exhibiting chiral smectic phases, such as smectic C* phases. Silanes of this invention can be chiral nonracemic, chiral racemic or achiral molecules. Chiral racemic and achiral silanes of this invention are useful alone or in combination as liquid crystal host materials. The materials of this invention can also be combined with known liquid crystal host materials to impart improved properties. Chiral nonracemic silanes of this invention can function as additives or dopants in host materials to impart chirality into the material. When introduced into host materials the silanes of this invention tend to broaden a smectic C phase and/or lower melting and/or freezing points of the material and to improve alignment of the material in a liquid crystal cell. Of particular interest are compounds of this invention which are disilanes.

Compounds of this invention comprise a silane tail which has the general formula:

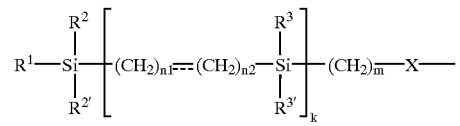

where:

R$^1$ is an alkyl or alkenyl group which may be straight-chain or branched having j (an integer greater than or equal to 1) carbon atoms and R$^2$, R$^{2'}$, R$^3$ and R$^{3'}$, independently of one another, are alkyl groups, particularly lower alkyl groups having from 1–6 carbon atoms, and more particularly are methyl and ethyl groups;

n1 and m are integers from 1 to about 20, and are not equal to zero; n2 may be zero or an integer to indicate the presence (an integer) or absence (zero) of a double or triple bond between the silicons, the dashed line indicates a possible double or triple bond (when either a double or triple bond is present the number of hydrogens on the adjacent carbons is decreased as needed); k is 0 or an integer from 1 to 10, preferably 0 or an integer from 1–4 and more preferably 0, 1 or 2;

k(n)+m+j preferably ranges from 6 to 20;

m, n and j are preferably 6–12; and

X is oxygen or a single bond.

Preferred liquid crystal silanes of this invention are those having a rod-like linear liquid crystal (mesogenic) core having 1, 2 or 3 rings and an alkyl, alkoxy or ether tail which can be fully or partially fluorinated.

Liquid crystal compounds of this invention include those having the structure:

Formula I

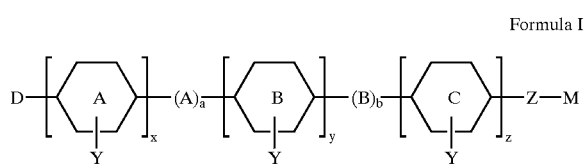

where:
D is the silane tail as defined above;
a, b, x, y, z can be 0 or 1 to indicate the presence or absence of a given structural element; x+y+z is 1, 2 or 3, when x is 0, a is 0; when z is 0, b is 0;
A and B, independently, when present, can be —O—, —COO—, —OOC—, —CH$_2$—CH$_2$—, —CH=CH— (cis or trans), —C≡C—, —CH=CH—CH=CH— (cis or trans), —O—CH$_2$— or —CH$_2$—O; when a or b is 0 the rings are linked through a single bond;
the A, B and C rings, independently of one another, are aromatic rings or alicyclic rings, preferred aromatic rings are 5 or 6 member rings, but one ring can be replaced with an aromatic fused ring moiety, e.g., naphthalene, or partially aromatic fused ring system, i.e., dehydronaphthalene; alicylic rings can have from 3–10 carbon atoms, and may be unsaturated, but cyclohexane or cyclohexene rings are preferred; with one or two of the A, B or C rings being alicylic (preferably cyclohexyl or cyclohexenyl rings); one or two carbons in the A, B or C rings that are aromatic can be replaced with a heteroatom, e.g., O, S, or N; one or two of the carbons in the A, B or C rings that are alicylic can be replaced with a heteroatom (e.g., N, S or O) or a C=O group;
Y indicates substitution on the rings of the core and can represent up to four substituents on aromatic rings and up to 10 substituents on cyclohexyl or cyclohexenyl rings; Y can for example be a halogen, CN group, NO$_2$, alkyl (lower having 1–6 carbons) or alkoxy (lower having 1–6 carbons), a preferred substituent is a halogen with fluorine more preferred;
Z is a single bond, an —O— or a —COO— or —OOC— group, preferred Z are single bonds and —O—; and
M is a tail group which can be:
a non-fluorinated alkyl, alkenyl or ether group or R$^F$, where R$^F$ is an alkyl, or ether group which is fully or partially fluorinated, these alkyl and/or ether groups may be straight-chain or branched; preferred M contain from 3–20 carbon atoms.
Any one, two or three of the A or B rings can be aromatic and are preferably selected from phenyl rings, pyridine or pyrimidine rings including 1,4-phenylene, 2,5-pyridinyl and 2,5-pyrimidyl rings, fluorinated 1,4-phenylenes, fluorinated phenylpyrimidyl and terphenyl. Exemplary aromatic cores are illustrated in Scheme 2. The D group or the Z—M or Z—R$^F$ group can be positioned on either side of the cores as illustrated in Scheme 2.
Phenyl rings can carry up to 4 substituents, e.g., up to four fluorines. Pyridine rings can carry up to 3 substituents, e.g., up to 3 fluorines. Pyrimidine rings can carry up to 2 substituents, e.g., up to 2 fluorines. Preferred rings are nonsubstituted phenyl rings, nonsubstituted pyrimidine rings and fluorinated phenyl rings. Preferred fluorinated phenyl rings carry one or two fluorines.
One or two of the A, B or C rings can be a cyclohexyl or cyclohexenyl group. Cores can contain one or two aromatic rings in combination with the cyclohexyl or cyclohexenyl rings. Preferred linker groups between aromatic rings and cyclohexyl or cyclohexenyl groups are —CH$_2$—CH$_2$—, —O—CH$_2$—, —CH$_2$—O—, —O—CO— or —CO—O— groups.

In a specific embodiment, compounds of this invention have the formula:

Formula II

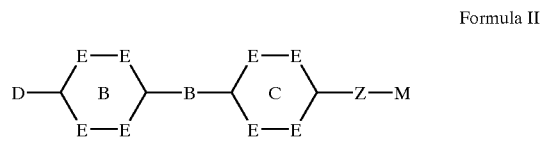

where D, M, B, Ring B and Ring C can take values as noted above and each E, independent of other E's, can be CH or CH$_2$, a nitrogen atom, CY or CHY, where Y is a CN, NO$_2$, an alkyl, a perhaloalkyl (e.g., perfluoroalkyl), or a halide, particularly a fluorine. Rings B and C can be alicyclic or aromatic and B and C that are aromatic can be fused ring systems, such as naphthalene. One of B or C can also be a fused ring system that is partially aromatic, such as a dehydronaphthalene ring system. In particular embodiments, both of rings B and C are aromatic, or one of B and C is aromatic and the other of B or C is alicyclic, particularly a cyclohexane or cyclohexene ring. In preferred embodiments: (1) all E's are CH; (2) one or two E's are N and the remaining E's are CH; (3) one or two E's are CF and the remaining E's are CH; (4) one or two E's are N, one or two E's are CF and the remaining E's are CH; (3) all E's on one ring are CH$_2$ and one, two or three E's on the other ring can be N or CF; (4) all E's on one ring are CH$_2$ and all E's on the other ring are CH.

In a further specific embodiment, compounds of this invention have the formula:

Formula III

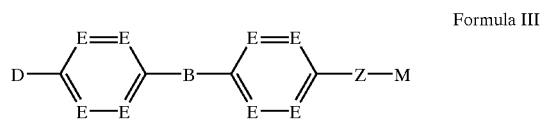

where each E independent of other E's can be CH or CY as defined above or a nitrogen atom and all other variables are as defined above. In preferred compounds of Formula III, all E's are CH or one or two E's can be CF or nitrogen with the remaining E's being CH. In preferred embodiments, the core is a phenylpyrimidine, a phenylpyridine, phenylbenzoate, biphenyl, or a terphenyl.

In another specific embodiment, compounds of this invention can have the formula:

Formula IV

where each E, independent of other E's, can be CH, CY or a nitrogen. In preferred compounds of Formula IV, all E's are CH or one or two E's can be CF or nitrogen with the remaining D's being CH.

In yet another specific embodiment, compounds of this invention can have the formula:

Formula V

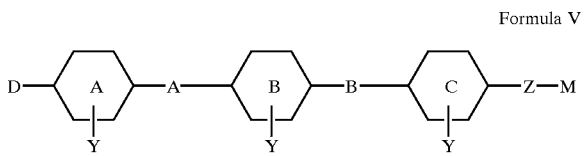

where variable have the values listed in Formula I above. In particular embodiments the core can be (1) an optionally substituted terphenyl, where the preferred substitution is one or two F's; (2) a core in which A or C is a cyclohexane or cyclohexene ring and the remaining rings are aromatic; (3) a core in which A or C is a cyclohexane or cyclohexene and the remaining rings are selected from phenyl rings, phenyl rings substituted with one or two F's, pyrimidine rings or pyridine rings; (4) a core in which A or C is a cyclohexane or cyclohexene and the remaining two rings represent a phenylpyrimidine, a phenylpyridine, a phenyl benzoate or a biphenyl.

Core structures can include, among others,:

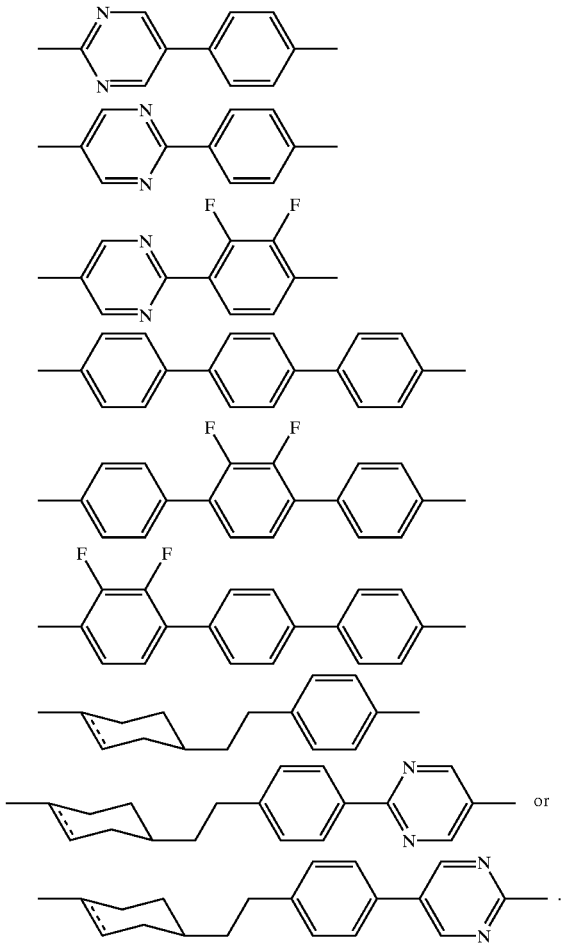

where the dashed line indicates the optional presence of a double bond. The silane D group and the —Z—M tails can be on either side of the cores as illustrated above. Additional exemplary cores of this invention are provided in Scheme 2.

M that is a non-fluorinated alkyl or ether group can be chiral nonracemic, chiral racemic or achiral. M may be branched chain or straight-chain. Preferred M have between 5 and 12 carbon atoms.

$R^F$ can be an alkyl group with one or more carbon atoms each substituted with 1–3 fluorines and with 1 or more non-neighboring carbons replaced with —O—(to give ethers and fluorinated ethers). $R^F$ can be chiral nonracemic, chiral racemic or achiral and can be straight-chain or branched.

Specific D groups include:

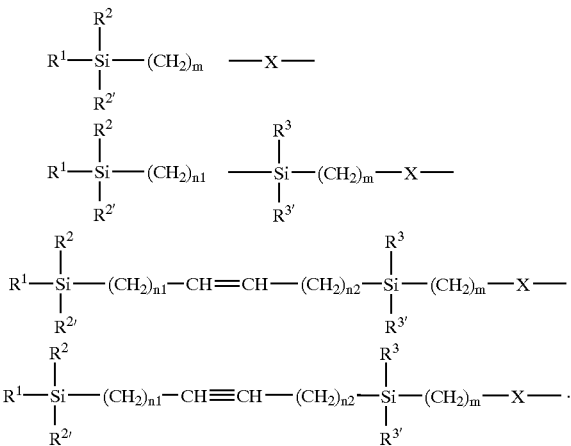

LC compositions of this invention include those comprising one or more compounds of the above Formulas I–V which exhibit a smectic C phase that extends over a temperature range of at least 30° C., as well as those which exhibit a smectic C phase that extends over a temperature range of at least 50° C. Compounds of this invention include those of the above formulas which exhibit both a smectic C phase and a smectic A phase. The presence of a smectic A phase in combination with a smectic C phase in an FLC composition facilitates alignment of the composition in an LC cell resulting in fewer layer defects and higher contrast devices. The presence of a nematic phase in addition to a smectic A and smectic C phase further facilitates alignment of the composition in an LC cell resulting in fewer layer defects and higher contrast devices. Compounds of this invention include those of the above formulas that do not themselves exhibit any liquid crystal phase, but which in combination with one or more LC compounds, including one or more LC compounds of this invention, exhibit liquid crystal phases, particularly smectic LC phases.

The invention provides LC compositions comprising one or more of the compounds of this invention as described above. LC compositions of the invention include those that contain sufficient amounts of one or more of the compounds of this invention to have a substantial effect upon the physical or optical properties of the LC composition in which they are combined or to which they are added. A substantial effect upon the physical or optical prosperities of the LC compositions includes, among others, a significant change in a LC property of the composition, birefringence, switching speed, alignment or contrast. LC compositions of this invention include those that contain from about 1% to 100% by weight of one or more compounds of this invention. LC compositions of this invention include those that contain 3% or more of one or more of the compounds of this invention. LC compositions of this invention include those that contain 5% or more of one or more of the compounds of this invention LC compositions of this invention include those that contain 10% or more of one or more of the compounds of this invention. LC compositions of this invention include those that contain 20% or more of one or more of the compounds of this invention. LC compositions of this invention include those that contain 25% or more of one or more of the compounds of this invention. LC compositions of this invention include those that contain 50% or more by weight of one or more of the compounds of this invention.

LC compositions of this invention include those that are ferroelectric liquid crystal compositions, particularly those that exhibit smectic phases, and more particularly those that exhibit a smectic A phase and/or a smectic C phase. LC compositions of this invention include those that comprise one or more of the compounds of this invention and which exhibit a smectic C phase that has a temperature range of 30° C. or more. LC compositions of this invention include those that comprise one or more compounds of this invention and which exhibit a smectic C phase that has a temperature range of 50° C. or more. In preferred compositions, the temperature range of the smectic C phase includes room temperature (about 20° C.). LC compositions of this invention include those comprising one or more compounds of this invention and which are chiral nonracemic. LC compositions of this invention include those comprising one or more compounds of this invention and which are chiral racemic or achiral. LC compositions of this invention also include those that consist essentially of two or more of the compounds of this invention and those in which the composition consists of a mixture of at least two of the compounds of this invention.

The invention includes FLC host mixtures that comprise one or more achiral or chiral racemic compounds of this invention, FLC host mixtures that consist essentially of one or more achiral or chiral racemic compounds of this invention and FLC host mixtures that consist of at least two achiral or chiral racemic compounds of this invention.

Addition of one or more compounds of this invention to mixtures of LC's can result in changes in physical or optical properties of those mixtures that make the resulting mixtures improved for applications in optical devices. In particular, the addition of one or more of the compounds of this invention can broaden the smectic C range of a given mixture. The addition of one or more of the compounds of this invention can improve alignment of a given LC or FLC mixture in a cell, leading to improved contrast in the optical device employing the LC or FLC cell. The addition of one or more of the compounds of this invention can lower the melting point and/or freezing point of a given mixture resulting in improved stability of the composition and longer shelf-life of devices containing the LC mixture. Of particular benefit, the compounds of this invention are compatible with (i.e., do not significantly detrimentally affect the properties of) LC and FLC materials that exhibit true bookshelf alignment. LC compounds exhibiting true bookshelf alignment are described for example in pending U.S. applications No. 60/229,892, filed Sep. 1, 2000 and Ser. No. 09/653,437 filed Sep. 1, 2000, which are incorporated by reference herein to provide examples of LC compounds which may be combined with the compounds of this invention to provide useful LC and FLC compositions. U.S. provisional applications Attorney Docket Nos. 106-00P and 86-00P, filed Dec. 15, 2000 also provide examples of LC compounds that may be combined with the compounds of the present invention to provide useful LC and FLC compositions. U.S. regular applications Attorney Docket Nos. 106-00 and 86-00 (commonly owned and concurrently filed with this application) and which take priority from the provisional applications filed Dec. 15, 2000 also provide examples of LC compounds that may be combined with the compounds of the present invention to provide useful LC and FLC compositions.

LC and FLC compositions of this invention are useful in the preparation of optical devices, particularly for optical switching devices and displays, including the preparation of SSFLC devices for use in displays. Those of ordinary skill in the art understand how to make LC and FLC cells and devices that utilize the compositions of this invention. In particular, methods and techniques are known and available in the art for alignment of LC and FLC compositions between substrate layers to form optical elements that exhibit true bistable, near bistable, or tristable state switching or optical elements that exhibit analog behavior. Various methods and techniques for constructing LC and FLC cells and for use of such cells are known in the art and can be readily adapted for use with compositions of this invention. The compositions of this invention are particularly well suited for providing devices that can operate (in a smectic C phase, for example) over a broad temperature range. The invention also provides LC devices comprising aligned layers of the LC compositions of this invention as switching elements. Of particular interest are SSFLC devices for use in various display applications.

DETAILED DESCRIPTION OF THE INVENTION

The invention relates generally to compounds that are useful as components in LC compositions. LC compositions typically contain a plurality of components, some of which themselves exhibit LC phases, which when combined exhibit LC phases. LC compositions of most interest are those which exhibit a desired LC phase over a temperature range that facilitates practical application of the composition in an optical device, e.g., the range contains room temperature. For example, LC materials exhibiting a smectic C range around normal room temperature can be employed in device applications. Preferred LC materials will exhibit the desired LC phase over a broad, useful temperature range which facilitates device stability.

Preferred LC materials will exhibit a desired LC phase with temperature range that minimizes or avoids crystallization of components of the LC composition during operation or storage of an optical device. Compounds of this invention can improve (broaden or shift) the temperature range of desired LC phases in LC compositions to which they are added. In particular, compounds of this invention can be employed to broaden or shift the temperature range of smectic C phases of LC compositions. The compounds may also be added to lower the temperature at which crystallization of an LC composition occurs to improve storage lifetime of an LC device containing the LC composition. Benefit is assessed as lowering of the melting point of the compositions and/or as lowering of the freezing point of the mixture. A significant improvement in LC stability can be obtained with even a 2° C. lowering of melting point, if that lowering is obtained without a significant negative effect on other LC properties. LC compositions of this invention include those in which the melting point of the LC composition is decreased by at least 4 or 5° C. by addition of one or more compounds of this invention withour signficant detrimental effect on other LC phase properties. In some compositions addition of 10 weight % or less of one or more compounds of this invention can achieve a lowering of 4 or 5° C. Significant improvements in LC stability can be achieved by lowering the freezing point of a mixture. LC compositions of this invention include those in which the freezing point of the LC composition is decreased by at least 5° C. or by at least 10° C. without signficant detrimental effect on other LC phase properties by addition of one or more compounds of this invention. Again in some compositions, an addition of 10 weight % of one or more compounds of this invention can achieve a lowering of the freezing point by 5° C. or 10 C. LC compositions comprising one or more of the compounds of this invention and exhibiting a freezing point of −60° C. or lower are of particular interest. Those compositions which exhibit a FP of −60° C. or lower and contain 10% by weight or less of a compound of this invention are particularly useful. LC compositions often exhibit a freezing point significantly lower than the melting point, indicative of supercooling. Preferred LC mixtures of this invention exhibit a freezing point that is significantly lower than the melting point of this invention. LC compositions of this invention include those in which the difference in the melting point and freezing point, i.e., |MP−FP| (absolute value of the difference of the MP and FP) of the composition is increased by 10° C. without significant detrimental effect on other LC phase properties by addition or one or more compounds of this invention. In some cases, an addition of 10 weight % of one or more compounds of this invention can result in a significant differential lowering, approaching 10° C., of FP compared to MP of a mixture.

Addition of one or more compounds of this invention to LC compositions can result in the introduction of beneficial LC phases. For example, addition of one or more compounds of this invention can result in the appearance of a smectic A phase above a smectic C phase. The presence of a smectic A phase is beneficial for alignment of LC compositions in LC cells to minimize defects and improve device contrast.

Compounds of this invention can impart additional beneficial optical or physical properties to LC compositions to which they are added. Properties that can be affected include: viscosity (decreased viscosity results in faster optical switching), tilt angle, birefringence, LC layer structure (the ability of the LC to form a desired layer structure, e.g., to form a true bookshelf structure), and alignment of layers between substrates (the ability of the LC to be aligned with minimal defects which are detrimental to device contrast). Preferred LC compositions of this invention include those in which addition of one or more compounds of this invention (Formulas I–V) results in a significant improvement of 10% or more in a physical or optical property of the mixture to which they are added.

Compounds of Formulas I–V are useful in the preparation of LC and FLC compositions which in turn are useful in various optical device applications.

Subsets of compounds of Formulas I–V that are useful in the preparation of LC and FLC compositions include those in which:
  the core is a phenylbenzoate, a biphenyl, a terphenyl, a phenyl pyrimidine, a phenylpyridine, a tolane or a biphenyl-phenyl, any of which may be substituted with one or two fluorines;
  the core contains two aromatic rings;
  the core contains two cyclohexane rings and one optionally substituted phenyl ring;
  the core contains one cyclohexene ring;
  both of X and Z are oxygen atoms;
  one of X or Z is an oxygen and the other is a single bond;
  X is oxygen and Z is a single bond;
  one or two of E in the core are CF;
  n1+n2+m+j is 5–12;
  n1+n2+m=j is 7–10;
  n2 is 0, j is 1 and n1 and m are 3, 4, 5 or 6;
  $R^1$, $R^2$, R1', $R^{2'}$, $R^3$ and $R^{3'}$ are all methyl groups;
  the core has one of the structures:

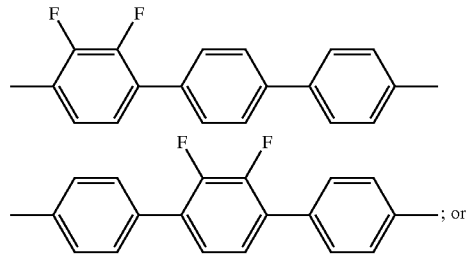

the core has one of the structures:

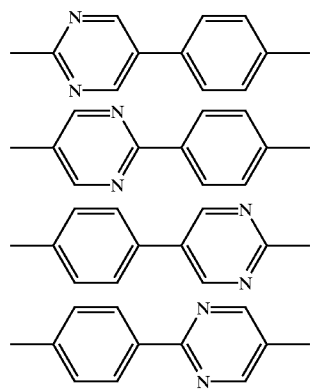

Compounds of this invention particularly useful in the preparation of LC compositions include those in which:
  the core is a phenyl pyrimidine (which may be substituted with one or two fluorines), X is oxygen, Z is an oxygen, and
  (1) $R^1$, $R^2$, R1', $R^{2'}$, $R^3$ and $R^{3'}$ are all methyl groups;
  (2) n1, n2 and m are 3–7;
  (3) n1, n2 and m are 4, 5 or 6;
  (4) n2 is 0, n1 and m are 3–7;
  (5) n 2 is 0, n1 and m are 4, 5, or 6;
  (6) n2 is 0 and n1+m is 8, 9 or 10;
  (7) M is $R^F$;
  (14) n2 is 0 and n1 is 1 or 2 and m is 3–6;
  (15) k is 0 and m is 5 to 12;
  (16) k is 0, m is 5 to 12, $R^1$, $R^2$, R1', $R^{2'}$, $R^3$ and $R^{3'}$ are all methyl groups;
  (17) k is 0, m is 5 to 12, $R^1$, $R^2$, R1', $R^{2'}$, $R^3$ and $R^{3'}$ are all methyl groups and X is O;
  (18) M is $R^F$ which is —$(CH_2)_p$—$(CF_2)_q$—O—$(CH_2)_r$—$(CF_2)_s$—[O—$(CH_2)_t$—$(CF_2)_u]_h$—W;
  (19) M is —$(CH_2)_v$—$C_wF_{2w+1}$; or
  (20) M is a non-fluorinated alkane or alkene;
Compounds of the invention useful in the preparation of LC compositions also include those in which:
  the core is phenyl pyrimidine; and one or both of X and Z are oxygen atoms and optionally other variables have the values listed in 1–20 above;
  the core is phenylpyridine; X is an oxygen atom and Z is a single bond and optionally other variables have the values listed in 1–20 above;
  the core is phenylpyridine; X and Z are both oxygen atoms and optionally other variables have the values listed in 1–20 above;

one or two of the E moieties of the core are a nitrogen atom and one or two are CF; X is an oxygen atom and Z is a single bond and optionally other variables have the values listed in 1–20 above;

the core is a phenylpyrimidine; X is an oxygen atoms; all of $R^1$, $R^2$, $R^{1'}$, $R^{2'}$, $R^3$ and $R^{3'}$ are methyl groups; n1+n2+j+m are 6–12 and other variables have the values listed in 1–20 above;

the core is a phenyl pyrimidine; X is an oxygen atoms; all of $R^1$, $R^2$, $R^{1'}$, $R^{2'}$, $R^3$ and $R^{3'}$ are methyl groups; n2 is 0 and n1+j+m are 6–12 and other variables have the values listed in 1–20 above;

the core is a phenyl pyrimidine; X is an oxygen atoms; all of $R^2$, $R^{1'}$, $R^{2'}$, $R^3$ and $R^{3'}$ are methyl groups; n2 is 0, n1 is 1, j is 1 to 6, m is 4 to 10 and other variables have the values listed in 1–20 above; or the core is phenyl pyrimidine; X is an oxygen atoms; all of $R^1$, $R^2$, $R^{1'}$, $R^{2'}$, $R^3$ and $R^{3'}$ are methyl groups; n2 is 0, n1 is 1, m is 4 to 10 and other variables have the values listed in 1–20 above.

Exemplary cores of compounds of this invention are listed in Scheme 2. The —Z—M and —D tails can be on either side of the cores as illustrated in Scheme 2.

Compounds of this invention can have a core with a single aromatic ring, e.g., a phenyl ring, a pyridine ring, or a pyrimidine ring, each of which can be optionally substituted with one to four substituents, particularly halides, CN, $NO_2$, alkyl, alkoxy, particularly lower alkyl and alkoxy, and more particularly F.

M can be a non-fluorinated alkyl or ether group or a fluorinated group $R^F$. M can, for example, have the structure:

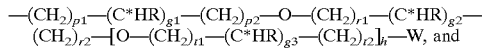

$R^F$ can, for example, have the structure:

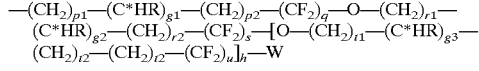

where each R, independent of R on other carbon atoms, is a hydrogen or an alky or a fluoroalkyl group, preferably a lower alkyl or lower fluoroalky group having from 1 to 6 carbon atoms, particularly methyl, ethyl, fluorinated ethyl, fluorinated methyl, perfluoroethyl or perfluoromethyl;

W is a hydrogen or fluorine;

h is 0 or an integer ranging from 1 to 10, inclusive, p1, p2, q, r1, r2, s, t1, t2, u are 0 or integers ranging from 1 to about 20, inclusive, and g1, g2, and g3 are either 1 or 0 and * indicates a potentially chiral carbon; preferably there are one or two asymmetric carbons in a chiral nonracemic tail.

In preferred embodiments, achiral M can have the structure:

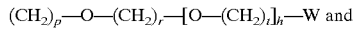

$R^F$ can have the structures:

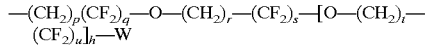

or

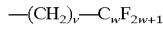

where h is 0 or an integer ranging from 1 to 10, inclusive, q, r, s, t, u, v, and w are 0 or integers ranging from 1 to about 20, inclusive; with p+q+r+s+h(t+u) preferably equal to 6 to about 20, inclusive, and v+w preferably equal to 6 to about 20, inclusive.

Chiral M and $R^F$ include an asymmetric carbon atom which is preferably within about 5 carbon atoms of the bond of the tail to the core ring. Exemplary chiral $R^F$ can have the structures:

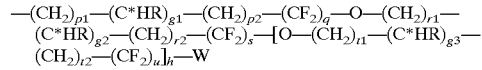

where R, W, h, p1, p2, q, r1, r2, s, t1, t2, u, g1, g2, and g3 are as defined above and there is only one asymmetric carbon; or

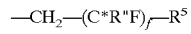

where f is an integer that can be 1, 2 or 3, R" is H or a lower alkyl or lower perfluoroalkyl (preferably H, $CH_3$ or $CF_3$) and $R^5$ is an alkyl, ether or fluorinated alkyl or fluorinated ether and * indicates an asymmetric carbon. Preferred chiral tails are those in which f is 1 or 2 and $R^5$ is an alkyl group.

Specific chiral tail groups include:

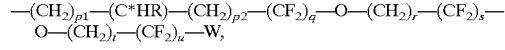

where p1 is 0–4, p2 is 0–10, q, r, s, t and u are 0–10, and p1+p2+q+r+s+t+u is preferably 6 to about 20, and R is preferably —$CH_3$ or —$CF_3$;

where $R^5$ is an alkyl group having 3 to about 20 carbon atoms; or

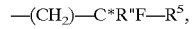

where $R^5$ is an alkyl group having 3 to about 20 carbon atoms.

Specific silane tail compounds of this invention are listed in Scheme 1.

As used herein the term alkyl refers generally to straight-chain and branched alkyl groups. Alkyl groups can include lower alkyl groups (those having from 1–6 carbon atoms) and higher alkyl groups (those having about 7 or more carbon atoms), unless otherwise noted. The term alkoxy group refers to groups having a terminal oxygen atom (—O-alkyl). For example, alkoxy tail groups are attached to the core via the terminal oxygen. The alkyl portion of an alkoxy group includes straight-chain and branched alkyl groups and unless otherwise noted includes lower alkyl and higher alkyl groups. Alkyl groups, including those of alkoxy group, typically have less than 20 carbons and preferably, dependent upon the specific structure, have 12 or fewer carbon atoms. In compounds where alkyl or alkoxy tail groups are specified, preferred alkyl groups have from 5 to 12 carbon atoms and more preferred alkyl groups have 6 to 10 carbon atoms.

The term alicyclic generally refers to alkyl or alkene groups that contain a cyclic portion. An alicyclic group can be a saturated ring or unsaturated ring, such as a cyclohexane or cyclohexene ring. Alicyclic rings can contain one or more (typically one) heteroatoms, e.g., O, N or S, in place of ring $CH_2$ groups. Further, one or more (typically one) ring $CH_2$ groups can be replaced with C=O groups. Alicyclic groups of the cores of this invention are optionally substituted (unless otherwise noted). Preferred substituents include lower alkyl groups, lower alkene groups, halogens, CN and NO$_2$ groups. Preferred halogen substituents are fluorines. In general, all, but two aromatic ring positions (e.g., the positions for linkages to tails or to other core rings) can carry non-hydrogen substitutents. However, more typically one or two ring positions (in addition to the linkages to the tails or other cores) can be substituted.

The term aromatic generally refers to a group containing at least one aromatic ring, e.g., a phenyl ring. Aromatic rings typically are have five or six-member aromatic rings. Aromatic rings can also include fused aromatic rings, such as naphthalene or dehydronapthalene rings (see Scheme 1). An aromatic ring can contain one or more (typically one or two) heteroatoms, e.g., O, N or S. Aromatic groups of the cores of this invention are optionally substituted (unless otherwise noted). Preferred substituents include lower alkyl groups, lower alkene groups, halogens, CN and NO$_2$ groups. Preferred halogen substituents are fluorines. In general, all, but two positions on the ring can be substituted (e.g., the positions for linkages to tails or to other core rings). However, typically one to four positions of the ring can be substituted and more typically one or two ring positions (in addition to the linkages to the tails or other cores) can be substituted. Preferred substituted aromatic rings have one position substituted with a lower alkyl or alkene group, a CN group or a NO$_2$ group. Additionally preferred substituted aromatic rings have one or two positions substituted with one or two halogens, and the preferred halogen is fluorine.

Compounds of this invention include compounds of Formulas I–V where:
  the core contains three aromatic rings;
  the core contains two aromatic rings and one alicyclic ring;
  the core contains one cyclohexane ring and one optionally substituted phenyl ring;

Exemplary silane compounds of this invention are illustrated in Scheme 1 as well in the accompanying pages of synthetic methods.

The invention provides LC compositions comprising one or more of the compounds of this invention as described above. LC compositions of the invention include those that contain sufficient amounts of the compounds of this invention to have a substantial effect upon the physical or optical properties of the LC composition to which they are added. LC compositions of this invention include those that contain from about 1% to 100% by weight of one or more compounds of this invention. LC compositions of this invention include those that contain 3% or more of one or more of the compounds of this invention. LC compositions of this invention include those that contain 5% or more of one or more of the compounds of this invention. LC compositions of this invention include those that contain 10% or more of one or more of the compounds of this invention. LC compositions of this invention include those that contain 20% or more of one or more of the compounds of this invention. LC compositions of this invention include those that contain 50% or more by weight of one or more of the compounds of this invention.

LC compositions of this invention include those that consist essentially of two or more of the compounds of this invention. LC compositions of this invention include those that are ferroelectric liquid crystal compositions, particularly those that exhibit smectic phases, and more particularly those that exhibit a smectic A phase and/or a smectic C phase. LC compositions of this invention include those that comprise one or more of the compounds of this invention and which exhibit a smectic C phase that has a temperature range of 30° C. or more. LC compositions of this invention include those that comprise one or more compounds of this invention and which exhibit a smectic C phase that has a temperature range of 50° C. or more. LC compositions of this invention include those comprising one or more compounds of this invention and which are chiral nonracemic. LC compositions of this invention include those comprising one or more compounds of this invention and which are chiral racemic or achiral.

Addition of one or more compounds of this invention to mixtures of LC's can result in changes in physical or optical properties of those mixtures that make the resulting mixtures improved for applications in optical devices. In particular, the addition of one or more of the compounds of this invention can broaden the smectic C range of a given mixture. The addition of one or more of the compounds of this invention can improve alignment of a given LC or FLCS mixture in a cell, leading to improved contrast in the optical device employing the LC or FLCS cell. Of particular benefit, the compounds of this invention are compatible with (i.e., do not significantly detrimentally affect the LC phase properties or phase configuration of LC and FLCS materials that exhibit true bookshelf alignment. LC compounds exhibiting true bookshelf alignment are described for example in pending U.S. applications No. 60/229,892, filed Sep. 1, 2000 and Ser. No. 09/653,437 filed Sep. 1, 2000, which are incorporated by reference herein to provide examples of LC compounds which may be combined with the compounds of this invention to provide useful LC and FLCS compositions.

Further, the addition of one or more of the compounds of this invention can in certain mixtures decrease the chevron angle, thus increasing boatwake threshold, as this term understood in the art. Moreover, the addition of one or more of the compounds of this invention can in certain mixtures lead to improvements in general bistability of the composition. Each of these effects can result in LC and FLCS cells having improved switching and optical properties.

U.S. provisional applications Attorney Docket Nos. 106-00P and 86-00P, filed concurrently herewith, also provide examples of LC compounds that may be combined with the compounds of the present invention to provide useful LC and FLC compositions. This invention includes LC compositions that combine one or more of the compounds of this invention with one or more compounds of the compounds of Attorney Docket No. 106-00P, those that combined one or more of the compounds of this invention with one or more of the compounds of Attorney Docket No. 86-00P; and those that combine one or more of the compounds of Attorney Docket No. 106-00P, one or more of the compounds of Attorney Docket No. 86-00P and one or more of the compounds of this invention.

LC and FLCS compositions of this invention are useful in the preparation of optical devices, particularly for optical switching devices and displays. Those of ordinary skill in the art understand how to make LC and FLCS cells and devices that utilize the compositions of this invention. Various methods and techniques for constructing LC and FLCS cells and for use of such cells are known in the art and can be readily adapted for use with compositions of this invention. The compositions of this invention are particularly well suited for providing devices that can operate (in a smectic C phase, for example) over a broad temperature range.

Specific examples of compounds of this invention are provided in Scheme 1 and in the Examples.

Exemplary methods for synthesizing the compounds of this invention are provided in the attached pages of examples. Compounds of this invention can be readily synthesized by methods that are well-known in the art, particularly in view of the guidance provided herein.

Exemplary LC mixtures comprising one or more compounds of this invention are provided in Tables 2–8 and 10–11. Properties of polarization, viscosity, electric rise time, resistivity, dielectric constant of these mixtures are given in Tables 1 and 9 as well as the melting point (MP) and freezing point (FP) as measured by differential scanning calorimetry. The lower temperature limit on the instrument used to provide FP measurements is −60° C., so table entries of FP of −60° C. indicate that the FP was less than or equal to −60° C. The properties listed in Tables 1 and 9 are measured using techniques that are well-known in the art. In these tables, I means "isotropic", N means nematic, A means smectic A, C means smectic C, Sx (or S?) means unidentified smectic phase, SI means smectic I and X means crystal. Structures of components are also given in Scheme 3. Chiral nonracemic LC mixtures for which data is provided in Table 1 include those comprising a compound of this invention in amounts ranging from about 4% by weight to about 8% by weight of the mixtures.

Table 9 provides the results of additional comparisons of properties of mixtures with and without addition of an alkene of this invention. MX 9387 is a mixture containing 3 weight % of MDW 1586 (Scheme 1) in base mixture 9533 (composition given in Table 10). MX 9530 is a mixture of 10 weight % MDW 1669 (Scheme 1) in base mixture 9532 (Table 11). MX 9387 exhibits a significant lowering of melting point (19° C.) compared to the base mixture (containing no alkene of this invention). Further, MX 9387 exhibits an increase of about 2° C. in the transition temperature from the smectic C to the smectic A phase compared to the base mixture. Note that the other LC properties of the mixture are not significantly effected by the addition of MDX 1598. Optical and switching properties of MX 9387 have not been optimized. MX 9530 exhibits a significant lowering of freezing point along with a significant decrease in MP compared to the base mixture (containing no alkene of this invention). Further, MX 9530 exhibits a smectic A phase in addition to the smectic C phase. The base mixture did not exhibit a smectic A phase. The presence of a smectic A phase is beneficial for obtaining good (minimal defect) alignment of LC layers between substrates in an LC cell. Note that the other LC properties of the mixture are not significantly effected by the addition of the exemplary compounds of this invention. Optical and switching properties of MX 9530 have not been optimized.

Scheme 4 provides exemplary components (1–20) that can be combined with one or more of the compounds of this invention to obtain useful LC and FLC compositions. Structures 9–13 and 17–20 illustrate components, including achiral or chiral racemic components, which can be combined with one or more of the compounds of this invention to obtain a LC mixture, particularly mixtures that exhibit smectic phases, and more particularly mixtures that exhibit smectic C phases and optionally smectic A phases. In such mixtures one or more of the silanes of this invention is combined with one or more of the compounds of structures 9–13 or 17–20. LC mixtures of this invention include those which combine one or more alkenes of this invention with one or more phenylpyrimidines of structure 9, and in particular include those which contain a total of about 2 to about 25 weight % of one or more compounds of this invention and a total of about 10–80 weight % of one or more compound of structure 9. LC mixtures of this invention also include those which combine one or more alkenes of this invention with one or more compounds of structures 11 and 12, and in particular include those which contain a total of about 2 to about 25 weight % of one or more compounds of this invention and a total of about 10 to about 40 weight % of one or more compounds of structures 11 and 12. LC mixtures of this invention also include those which combine one or more alkenes of this invention with one or more compounds of structure 10 and in particular include those which contain a total of about 2 to about 25 weight % of one or more compounds of this invention and a total of about 5 to about 50 weight % of one or more compounds of structure 10. Of particular interest are mixtures which contain at least three terphenyl compounds each of which is substituted with two fluorines on a different ring of the core. The use of such terphenyl compounds in LC compositions is described in U.S. Pat. No. 5,278,680, which is incorporated by reference herein. LC mixtures of this invention can further contain one or more compounds of structure 13, and in particular can contain from about 5 to about 15 weight % of one or more compounds of structure 13. LC mixtures of this invention can combine components of structure 9, components of structures 11 or 12, components of structure 10 and optionally components of structure 13 with one or more alkenes of this invention.

Structures 17–20 (in Scheme 4) illustrate exemplary chiral non-racemic components that can be employed to prepare chiral nonracemic LC mixtures, particularly those chiral nonracemic LC mixtures that exhibit smectic phases. Chiral nonracemic enantiomers of the compounds of structures 17–20 can also be employed in the mixtures of this invention. Chiral nonracemic compounds useful in LC compositions of this invention include those which have an achiral tail that is a partially fluorinated tail, e.g., a tail with a terminal portion that is a perfluoroalkyl group, i.e., a tail that has the formula: $-O-C_nH_{2n}-C_mCF_{m+1}$, where n+m ranges from 3 to 20 and more preferably is 5 to 12. Introduction of an achiral tail that is partially fluorinated into a chiral nonracemic compound results in a high polarization dopant compound which when added to LC host compositions gives significant enhancement of polarization of that composition. LC compositions of this invention include those which contain one or more of the silane compounds of this invention in combination with up to a total of about 25% by weight of one or more of compounds 17–20 of Scheme 4. LC compositions further include those which combine one or more compounds of structure 9, one or more compounds of structure 10, or one or more compounds of structures 11 or 12 with one or more alkene compounds of this invention and one or more of the chiral nonracemic compounds of structures 17–20. Chiral nonracemic compounds of this invention can also include one or more compounds of structure 13, one or more compounds of structures 14–16 and one or more compounds of structures 1–8.

Compounds of structures 1–20 can be prepared by methods that are well known in the art from readily available starting materials. Methods that are useful in the preparation of various LC compounds and FLC compounds are provided, for example in U.S. Pat. Nos.: 5,051,506; 5,061, 814; 5,130,048; 5,167,855; 5,178,791; 5,178,793; 5,180, 520; 5,271,864; 5,278,680; 5,380,460; 5,422,037; 5,453, 218; 5,457,235; 5,539,555; 5,543,078; 5,585,036; 5,626, 792; 5,637,256; 5,658,493; 5,753,139; 5,866,036; and 6,139,771. Each of which is incorporated by reference herein for synthetic methods applicable to the synthesis of compounds of this invention including compounds of structures 1–20. Concurrently filed U.S. provisional application Attorney Docket No. 75-99 provides high polarization dopants with partially fluorinated tails that are useful in LC compositions of this invention. Compounds of structures 18 and 20 are described therein. This provisional application is incorporated by reference herein for its disclosure of such dopants. The listed patents along with U.S. Pat. Nos. 5,168,381 and 5,596,434 also provide detail of how LC and FLC compositions of this invention can be applied for the production of LC cells and optical devices.

The following examples are intended to further illustrate the invention and are not intended to limit the scope of the invention.

EXAMPLES

Compound 1

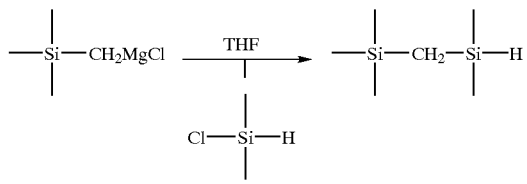

1. Dimethylsilanyltrimethylsianlylmethane

A solution of (trimethylsilyl)methylmagnesium chloride (50.0 ml, 50 mmol, in THF) was added dropwise to a solution of cholorodimethylsilane (4.73 g, 50 mmol) in THF (50 ml) at 0° C. under an atmosphere of dry nitrogen. The reaction mixture was stirred overnight and distilled to yield a clear, colorless oil.

Yield: 6.90 g, 47.3 mmol. 95%

Boiling point: 85–87 degree C. 1 atmosphere.

Compound 2

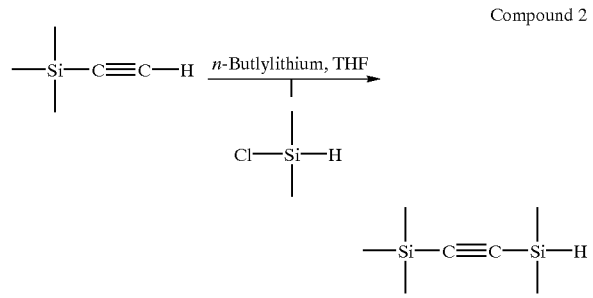

2. Dimethylsilanyltrimethylsianlylethyne

A solution of n-butyllithium (15.0 ml, 37.5 mmol, 2.5 M in hexanes) was added dropwise to a stirred, cooled (−78° C.) solution of (trimethylsilyl)acetylene (3.68, 37.5 mmol) in THF (80 ml) under an atmosphere of dry nitrogen. The reaction mixture was maintained at −78° C. for 1.5 h and a solution of chlorodimethylsilane (3.55 g, 37.5 mmol) in THF (20 ml) was added dropwise. The reaction mixture was allowed to warm to room temperature, washed with water and the organic layer extracted into ethyl hexane (3 times). The combined extracts were washed with brine, dried (MgSO$_4$) and the solvent removed in vacuo to yield a clear oil, which was purified by distillation.

Yield: 5.62 g, 36.0 mmol, 96%

Analysis by NMR indicated a complete reaction, b. pt. 85–87 degrees C.

Compound 3

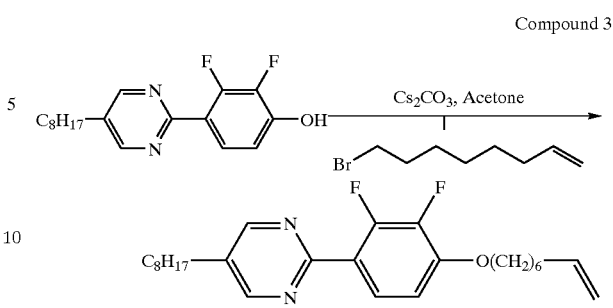

3. 2-(2,3-Difluoro-4-oct-7-enyloxyphenyl)-5-octylpyrimidine

A suspension of 2-(2,3-difluoro-4-hydroxyphenyl)-5-octylpyrimidine (1.00 g, 3.07 mmol), 8-bromo-1-octene (0.59 g, 3.07 mmol) and cesium carbonate (1.99 g, 6.14 mmol) in acetone (70 ml) was heated under reflux for 18 h. The reaction mixture was cooled to room temperature, washed with water and the organic layer extracted in ethyl acetate/hexane (3 times, 1:1). The combined extracts were washed with brine, dried (MgSO$_4$) and the solvent removed in vacuo. The residues were purified by column chromatography [silica gel, eluted with hexane/ethyl acetate (4:1), R$_f$ 0.30] and recrystallized from hexane to yield colorless crystals.

Yield: 1.29 g, 2.96 mmol, 96%

Transitions: Cr (28.5 SmC) 30.4 N 33.9 I° C.

Compound 4

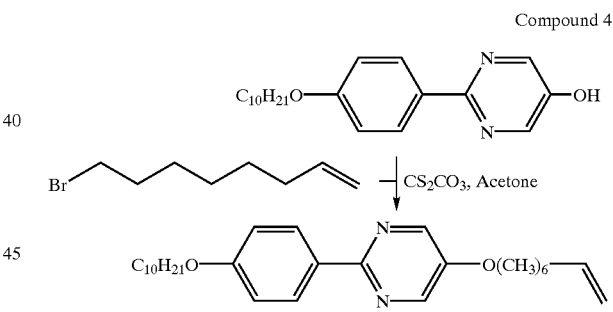

4. 5-Decyloxy-2-(4-oct-7-enyloxyphenyl)pyrimidine

A suspension of 2-(4-hydroxyphenyl)pyrimidine (1.89 g, 5.76 mmol), 8-bromo-1-octene (1.00 g, 5.24 mmol) and cesium carbonate (3.74 g, 11.52 mmol) in acetone (50 ml) was heated under reflux for 12 h. The reaction mixture was cooled to room temperature, washed with water and the organic layer extracted into ethyl acetate/hexane (3 times, 1:1). The combined organic extracts were washed with brine, dried (MgSO$_4$) and the solvent removed in vacuo. The residues were purified by column chromatography [silica gel eluted with hexane/ethyl acetate (9:1), R$_f$ 0.47] and recrystallized from ethanol to yield colorless crystals.

Yield: 2.22 g, 5.07 mmol, 97%

Transitions: Cr 51.3 SmA 68.8 I

Compound 5

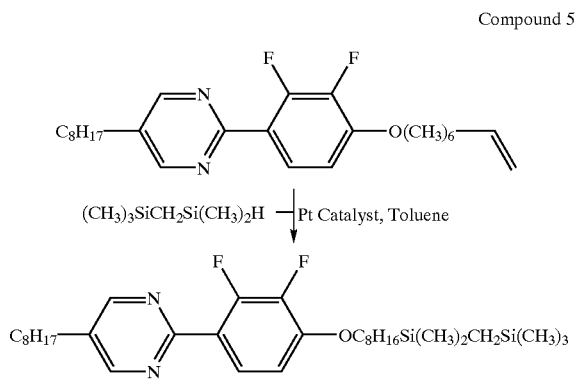

5. 2-{4-[8-(Dimethyltrimethylsilanylmethylsilanyl)-octyloxy]-2,3-difluorophenyl}-5-octylpyrimidine A solution of compound 1 (0.436 g, 1.00 mmol), compound 3 (0.158 g, 1.10 mmol) and hexachloroplatinic acid (20.0 μl, 8.9 mol dm$^{-3}$, 0.178 mmol) in toluene (40 ml) was heated at 60° C. for 48 h under an atmosphere of dry nitrogen. The reaction mixture was cooled to room temperature and the solvent removed in vacuo. The residues were purified by column chromatography [silica gel, eluted with hexane/ethyl acetate (4:1), $R_f$ 0.54] and recrystallized from hexane to yield colorless crystals.

Yield: 0.48 g, 0.83 mmol, 83%

Transitions: Cr 36.0 SmC 41.6 N 47.7 I° C.

Compound 6

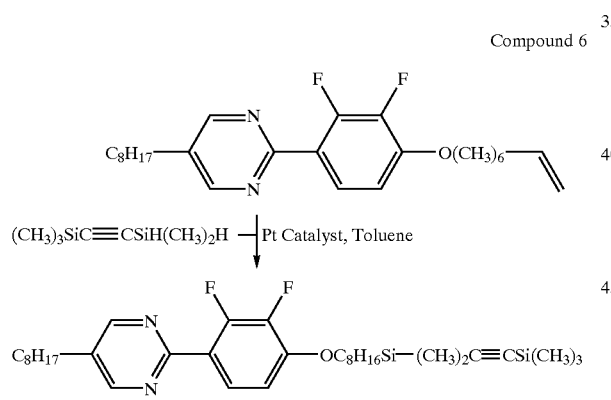

6. 2-{4-[8-(Dimethyltrimethylsilanylethynyllsilanyl)-octyloxy]-2,3-difluorophenyl}-5-octylpyrimidine A solution of compound 2 (0.036 g, 0.232 mmol), compound 3 (0.100 g, 0.232 mmol) and hexachloroplatinic acid (10.0 μl, 8.9 mol dm$^{-3}$, 0.09 mmol) in toluene (40 ml) was heated at 60° C. for 48 h under an atmosphere of dry nitrogen. The reaction mixture was cooled to room temperature and the solvent removed in vacuo. The residues were purified by column chromatography [silica gel, eluted with hexane/ethyl acetate (4:1), $R_f$ 0.52] and recrystallized from hexane to yield colorless crystals.

Yield: 0.11 g, 0.19 mmol, 83%

Transitions: Cr 25.8 SmC 30.1 N 36.0 I° C.

Compound 7

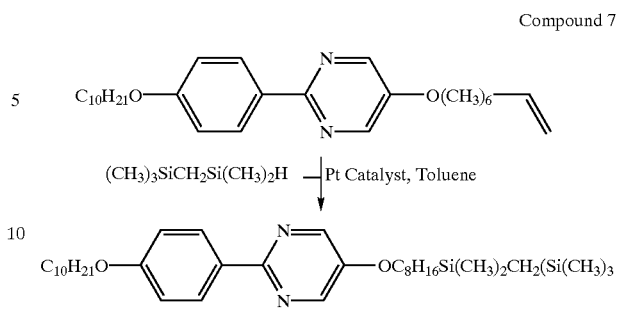

7. 5-Decyloxy-2-{4-[8-(Dimethyltrimethylsilanyl-methylsilanyl)-octyloxy]-2,3-difluorophenyl}pyrimidine A solution of compound 1 (0.073 g, 0.500 mmol), compound 4 (0.225 g, 0.500 mmol) and hexachloroplatinic acid (20.0 μl, 8.9 mol dm$^{-3}$, 0.178 mmol) in toluene (40 ml) was heated at 60° C. for 48 h under an atmosphere of dry nitrogen. The reaction mixture was cooled to room temperature and the solvent removed in vacuo. The residues were purified by column chromatography [silica gel, eluted with hexane/ethyl acetate (4:1), $R_f$ 0.46] and recrystallized from hexane to yield colorless crystals.

Yield: 0.296 g, 0.499 mmol, 99%

Transitions: Cr 51.3 SmC 89.5 SmA 101.4 I° C.

Compound 8

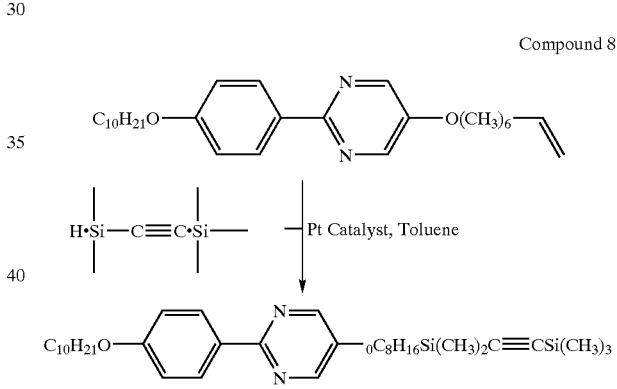

8. 5-Decyloxy-2-{4-[8-(Dimethyltrimethylsilanylethynyl-silanyl)-octyloxy]-2,3-difluorophenyl}pyrimidine A solution of compound 2 (0.090 g, 0.58 mmol), compound 4 (0.254 g, 0.58 mmol) and hexachloroplatinic acid (20.0 μl, 8.9 mol dm$^{-3}$, 0.178 mmol) in toluene(40 ml) was heated at 60° C. for 48 h under an atmosphere of dry nitrogen. The reaction mixture was cooled to room temperature and the solvent removed in vacuo. The residues were purified by column chromatography [silica gel, eluted with hexane/ethyl acetate (9:1), $R_f$ 0.33] and recrystallized from hexane to yield colorless crystals.

Yield: 0.295 g, 0.497 mmol, 86%

Transitions: Cr 46.8 SmC 80.5 SmA 90.8 I° C.

Compound 9

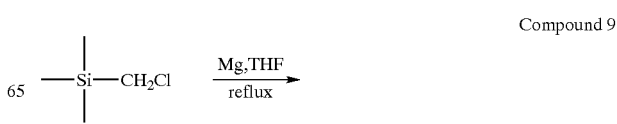

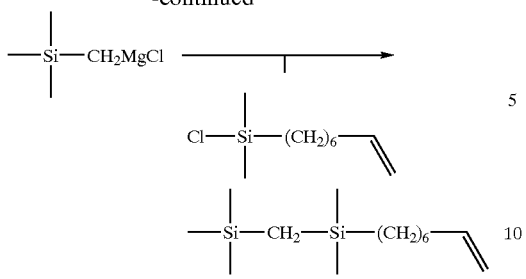

9. 8-(Dimethylsilanylmethyltrimethylsilanyl)oct-1-ene

A solution of chloromethyltrimethylsilane (6.79 g, 55.0 mmol) in THF (50 ml) was added dropwise to a stirred suspension of magnesium (1.58 g, 65.0 mmol) under an atmosphere of dry nitrogen. The reaction mixture was heated under relux for 0.5 h, cooled to room temperature and the reaction mixture canulated into a solution of chlorodimethyloct-7-enesilane (10.28 g, 50 mmol) in THF (50 ml) and the reaction stirred at room temperature for 24 h. A solution of hydrochloric acid (50 ml, 5%) was added in three portions and the mixture stirred for 0.5 h. The reaction mixture was washed with water and the organic layer extracted in to hexane (3×30 ml), the combined extracts were washed with brine, dried (MgSO$_4$) and the solvent removed in vacuo to yield a colorless oil.

Yield: 11.52 g, 45 mmol, 90%

Compound 10

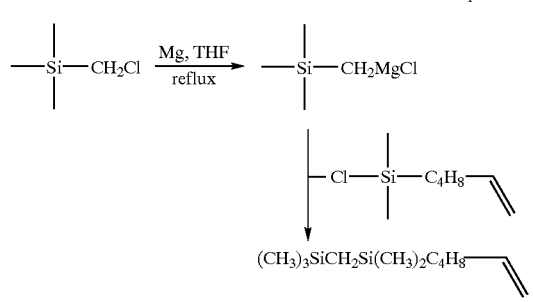

10. 6-(Dimethylsilanylmethyltrimethylsilanyl)hex-1-ene

A solution of chloromethyltrimethylsilane (6.21 g, 50.3 mmol) in THF (50 ml) was added dropwise to a stirred suspension of magnesium (1.45 g, 60.0 mmol) under an atmosphere of dry nitrogen. The reaction mixture was heated under relux for 0.5 h, cooled to room temperature and the reaction mixture canulated into a solution of chlorodimethylhex-5-enesilane (8.072 g, 50 mmol) in THF (50 ml) and the reaction stirred at room temperature for 24 h. A solution of hydrochloric acid (50 ml, 5%) was added in three portions and the mixture stirred for 0.5 h. The reaction mixture was washed with water and the organic layer extracted in to hexane (3×30 ml), the combined extracts were washed with brine, dried (MgSO$_4$) and the solvent removed in vacuo to yield a colorless oil.

Yield: 6.79 g, 30.86 mmol, 65%

Compound 11

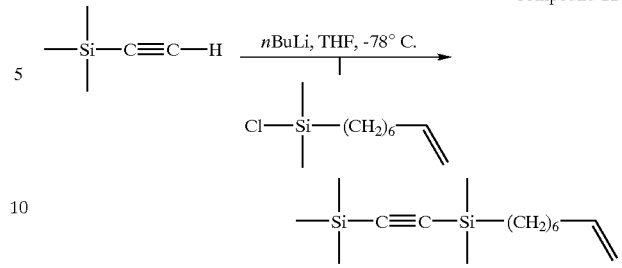

11. 8-(Dimethylsilanylethynylltrimethylsilanyl)oct-1-ene

A solution of nbutyllithium (40 ml, 0.100 mol, 2.5 mol dm$^{-3}$ in hexanes) was added dropwise to a stirred, cooled (−78° C.) solution of trimethylsilylacetylene (9.80 g, 0.100 mol) in THF (60 ml) under an atmosphere of dry nitrogen. The reaction mixture was stirred for 2 h at −78° C. and a solution of chlorodimethyloct-7-enesilane (20.55 g, 0.100) added dropwise. The reaction mixture was allowed to warm to room temperature overnight, washed with water and the organic layer extracted into hexane (3×40 ml). The combined extracts were washed with brine, dried (MgSO$_4$) and the solvent removed in vacuo to yield a clear oil.

Yield: 22.88 g, 0.086 mol, 86%

Compound 12

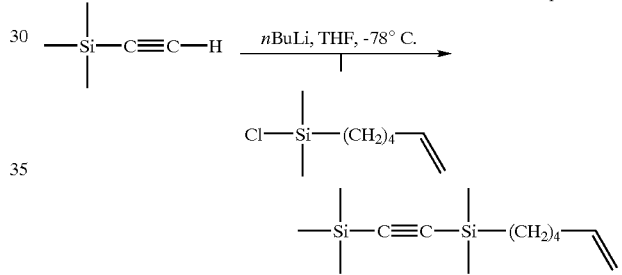

12. 6-(Dimethylsilanylethynylltrimethylsilanyl)hex-1-ene

A solution of nbutyllithium (40 ml, 0.100 mol, 2.5 mol dm$^{-3}$ in hexanes) was added dropwise to a stirred, cooled (−78° C.) solution of trimethylsilylacetylene (9.80 g, 0.100 mol) in THF (60 ml) under an atmosphere of dry nitrogen. The reaction mixture was stirred for 2 h at −78° C. and a solution of chlorodimethyloct-7-enesilane (20.55 g, 0.100) added dropwise. The reaction mixture was allowed to warm to room temperature overnight, washed with water and the organic layer extracted into hexane (3×40 ml). The combined extracts were washed with brine, dried (MgSO$_4$) and the solvent removed in vacuo to yield a clear oil.

Yield: 24.27 g, 91.2 mmol, 91%

Compound 13

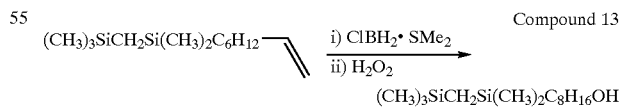

13. 8-(Dimethylsilanylmethyltrimethylsilanyl)octan-1-ol

Monochloroborane-methyl sulfide (1.10 ml, 1.16 g, 10.5 mmol) was added dropwise to a stirred, cooled (0° C.) solution of compound 9 (2.56 g, 10.0 mmol) in THF (30 ml). The reaction mixture was stirred at 0° C. for 24 h, and a solution of hydrogen peroxide (10 ml, 30% in water) added dropwise and the reaction mixture stirred at 0° C. for 4 h, washed with water and the organic layer extracted into hexane/ethyl acetate (3×30 ml, 1:1). The combined extracts were washed with brine, dried (MgSO₄) and the solvent removed in vacuo to yield colorless oil. The crude product was purified by column chromatography [silica gel eluted with hexane/ethyl acetate (4:1)] to yield a colorless oil.

Yield: 1.525 g, 5.57 mmol, 56%

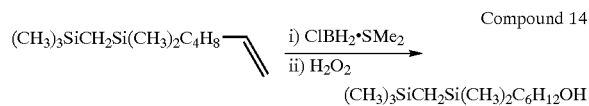

Compound 14

14. 6-(Dimethyltrimethylsilanylmethylsilanyl)-hexan-1-ol

Monochloroborane-methyl sulfide (2.03 ml, 2.15 g, 19.5 mmol) was added dropwise to a stirred, cooled (0° C.) solution of compound 10 (2.96 g, 13.0 mmol) in THF (20 ml). The reaction mixture was stirred at 0° C. for 24 h, and a solution of hydrogen peroxide (13 ml, 30% in water) added dropwise and the reaction mixture stirred at 0° C. for 4 h, washed with water and the organic layer extracted into hexane/ethyl acetate (3×30 ml, 1:1). The combined extracts were washed with brine, dried (MgSO₄) and the solvent removed in vacuo to yield colorless oil. The crude product was purified by column chromatography [silica gel eluted with hexane/ethyl acetate (4:1)] to yield a colorless oil.

Yield: 1.41 g, 5.73 mmol, 44%

Compound 15

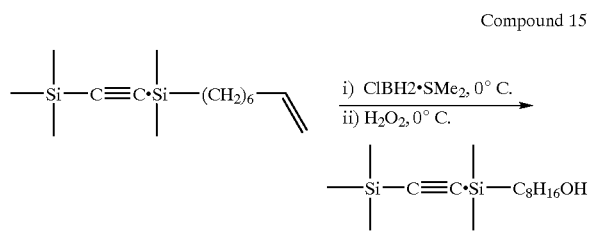

15. 8-(Dimethyl-trimethylsilanylethynyl-silanyl)-octan-1-ol

Monochloroborane-methyl sulfide (14.09 g, 0.1275 mol) was added dropwise to a stirred, cooled (0° C.) solution of compound 11 (22.60 g, 0.085 mol) in THF (30 ml). The reaction mixture was stirred at 0° C. for 24 h, and a solution of hydrogen peroxide (90 ml, 30% in water) added dropwise and the reaction mixture stirred at 0° C. for 4 h, washed with water and the organic layer extracted into hexane/ethyl acetate (3×40 ml, 1:1). The combined extracts were washed with brine, dried (MgSO₄) and the solvent removed in vacuo to yield colorless oil. The crude product was purified by column chromatography [silica gel eluted with hexane/ethyl acetate (4:1)] to yield a colorless oil.

Yield: 15.21 g, 0.0535 mol, 63%

Compound 16

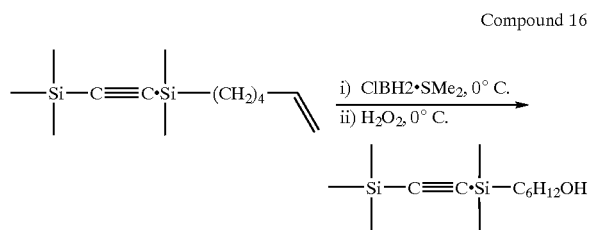

16. 6-(Dimethyl-trimethylsilanylethynyl-silanyl)-hexan-1-ol

Monochloroborane-methyl sulfide (16.58 g, 0.150 mol) was added dropwise to a stirred, cooled (0° C.) solution of compound 12 (23.80 g, 0.085 mol) in THF (30 ml). The reaction mixture was stirred at 0° C. for 24 h, and a solution of hydrogen peroxide (105 ml, 30% in water) added dropwise and the reaction mixture stirred at 0° C. for 4 h, washed with water and the organic layer extracted into hexane/ethyl acetate (3×45 ml, 1:1). The combined extracts were washed with brine, dried (MgSO₄) and the solvent removed in vacuo to yield colorless oil. The crude product was purified by column chromatography [silica gel eluted with hexane/ethyl acetate (4:1)] to yield a colorless oil.

Yield: 18.18 g, 0.071 mol, 71%

Compound 17

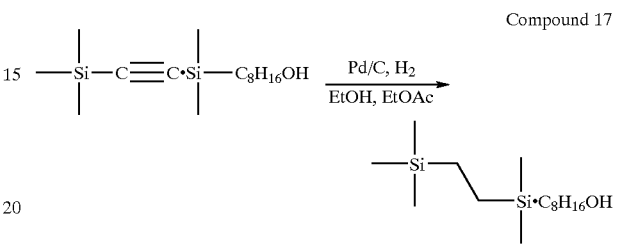

17. 8-[Dimethyl-(2-trimethylsilanyl-ethyl)-silanyl]-octan-1-ol

A suspension of compound 15 (15.21 g, 0.0535 mol) and palladium hydroxide on charcoal (1.85 g, 1.60 mmol) in ethanol and ethyl acetate (120 ml, 1:1) was stirred under an atmosphere of hydrogen for 24 h at room temperature. The reaction mixture was filtered (celite) and the solvent roved in vacuo to yield a clear oil.

Yield: 15.41 g, 0.0535 mol, 100%

Compound 18

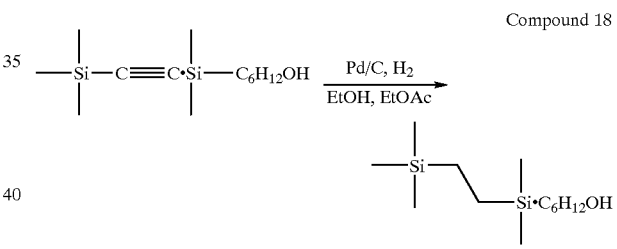

18. 6-[Dimethyl-(2-trimethylsilanyl-ethyl)-silanyl]-hexan-1-ol

A suspension of compound 16 (18.18 g, 0.071 mol) and palladium hydroxide on charcoal (2.46 g, 2.13 mmol) in ethanol and ethyl acetate (120 ml, 1:1) was stirred under an atmosphere of hydrogen for 24 h at room temperature. The reaction mixture was filtered (celite) and the solvent roved in vacuo to yield a clear oil.

Yield: 18.46 g, 0.071 mol, 100%

Compound 19

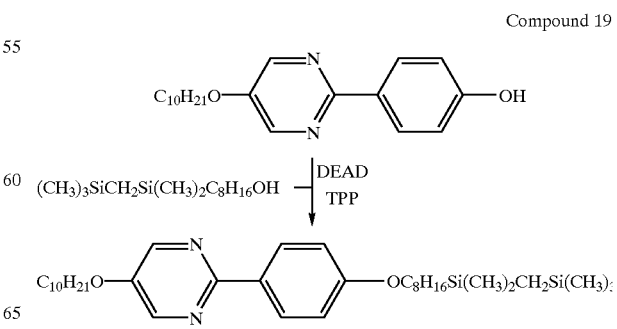

19. 5-Decyloxy-2-{4-[8-(dimethyl-trimethylsilanylmethyl-silanyl)-octyloxy]-phenyl}-pyrimidine A solution of diethylazodicarboxylate (0.087 g, 0.500 mmol) in THF (5.0 ml) was added dropwise to a stirred solution of 4-(5-decyloxy-pyrimidin-2-yl)-phenol (0.131 g, 0.40 mmol), compound 13 (0.110 g, 0.400 mmol) and triphenylphosphine (0.131 g, 0.500 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.0.105 g, 0.180 mmol, 45%

Transitions:

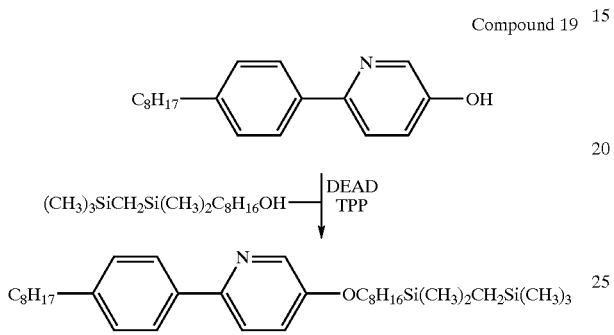

Compound 19

20. 5-[8-(Dimethyl-trimethylsilanylmethyl-silanyl)-octyloxy]-2-(4octylphenyl)-pyridine A solution of diethylazodicarboxylate (0.087 g, 0.500 mmol) in THF (5.0 ml) was added dropwise to a stirred solution of 6-(4-Octyl-phenyl)-pyridin-3-ol (0.113 g, 0.40 mmol), compound 13 (0.110 g, 0.400 mmol) and triphenylphosphine (0.131 g, 0.500 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.102 g, 0.184 mmol, 46%

Transitions:

Compound 21

21. 5-[8-(Dimethyl-trimethylsilanylmethyl-silanyl)-octyloxy]-2-(3-fluoro-4-octyloxyphenyl)-pyridine A solution of diethylazodicarboxylate (0.087 g, 0.500 mmol) in THF (5.0 ml) was added dropwise to a stirred solution of 6-(3-fluoro-4-octylphenyl)-pyridin-3-ol (0.120 g, 0.40 mmol), compound 13 (0.110 g, 0.400 mmol) and triphenylphosphine (0.131 g, 0.500 mmol) in THF (10 ml). The treaction mixture was stirred at room temperature for 24 h, the solvent removed in vacuo and the residues purified by column chromatography [silica gel eluted with hexane/ethyl acetate (9:1)] to yield a clear oil.

Yield: 0.102 g, 0.208 mmol, 46%

Compound 22

22. 2-{4-[8-(Dimethyl-trimethylsilanylmethyl-silanyl)-octyloxy]-phenyl}-5-octyl-pyrimidine A solution of diethylazodicarboxylate (0.087 g, 0.500 mmol) in THF (5.0 ml) was added dropwise to a stirred solution of 4-(5-decylpyrimidin-2-yl)-phenol (0.125 g, 0.40 mmol), compound 13 (0.110 g, 0.400 mmol) and triphenylphosphine (0.131 g, 0.500 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.126 g, 0.222 mmol, 56%

Transitions:

Compound 23

23. 5-Decyl-2-{4-[8-(dimethyl-trimethylsilanylmethyl-silanyl)-octyloxy]-phenyl}-pyrimidine A solution of diethylazodicarboxylate (0.087 g, 0.500 mmol) in THF (5.0 ml) was added dropwise to a stirred solution of 4-(5-octylpyrimidin-2-yl)-phenol (0.114 g, 0.40 mmol), compound 13 (0.110 g, 0.400 mmol) and triphenylphosphine (0.131 g, 0.500 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.112 g, 0.207 mmol, 52%

Transitions:

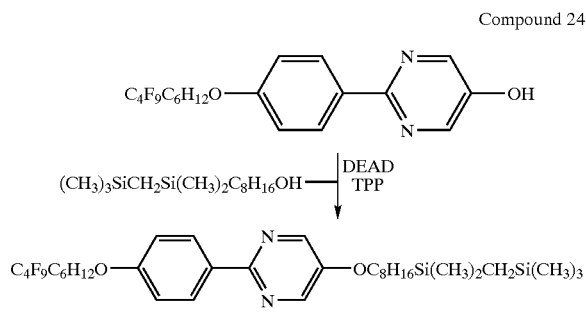

Compound 24

24. 5-[8-(Dimethyl-trimethylsilanylmethyl-silanyl)-octyloxy]-2-[4-(7,7,8,8,9,9,10,10,10-nonafluorodecyloxy)-phenyl]-pyrimidine A solution of diethylazodicarboxylate (0.044 g, 0.250 mmol) in THF (5.0 ml) was added dropwise to a stirred solution of 2-[4-(7,7,8,8,9,9,10,10,10-nonafluorodecyloxy)-phenyl]-pyrimidin-5-ol (0.098 g, 0.20 mmol), compound 13 (0.055 g, 0.200 mmol) and triphenylphosphine (0.0655 g, 0.250 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.102 g, 0.104 mmol, 52%

Transitions:

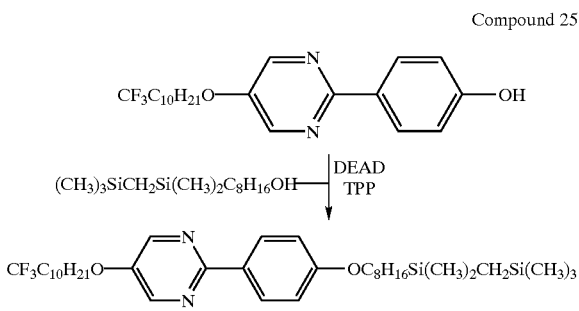

Compound 25

25. 2-{4-[8-(Dimethyl-trimethylsilanylmethyl-silanyl)-octyloxy]-phenyl}5-(11,11,11-trifluoroundecyloxy)-pyrimidine A solution of diethylazodicarboxylate (0.0544 g, 0.313 mmol) in THF (5.0 ml) was added dropwise to a stirred solution of 4-[5-(11,11,11-trifluoroundecyloxy)-pyrimidin-2-yl]-phenol (0.099 g, 0.250 mmol), compound 13 (0.0685 g, 0.250 mmol) and triphenylphosphine (0.0820 g, 0.313 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.051 g, 0.0774 mmol, 31%

Transitions:

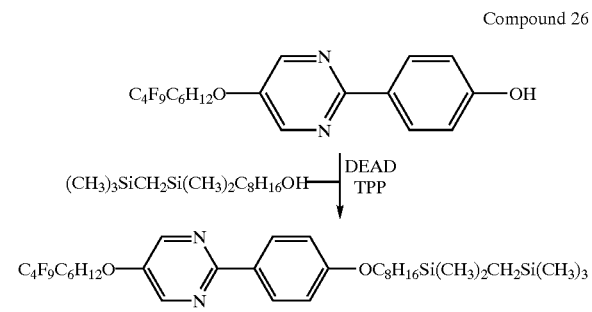

Compound 26

26. 2-{4-[8-(Dimethyl-trimethylsilanylmethyl-silanyl)-octyloxy]-phenyl}-5-(7,7,8,8,9,9,10,10,10-nonafluorodecyloxy)-pyrimidine A solution of diethylazodicarboxylate (0.0435 g, 0.250 mmol) in THF (5.0 ml) was added dropwise to a stirred solution of 4-[5-(7,7,8,8,9,9,10,10,10-nonafluorodecyloxy)-pyrimidin-2-yl]-phenol (0.098 g, 0.200 mmol), compound 13 (0.548 g, 0.200 mmol) and triphenylphosphine (0.0655 g, 0.250 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.108 g, 0.119 mmol, 60%

Transitions:

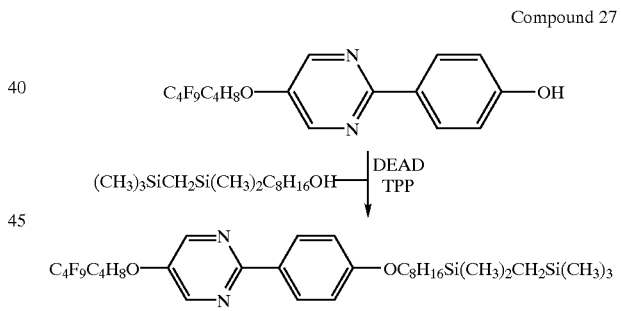

Compound 27

27. 2-{4-[8-(Dimethyl-trimethylsilanylmethyl-silanyl)-octyloxy]-phenyl}-5-(5,5,6,6,7,7,8,8,8-nonafluorooctyloxy)-pyrimidine A solution of diethylazodicarboxylate (0.871 g, 5.00 mmol) in THF (5.0 ml) was added dropwise to a stirred solution of 4-[5-(5,5,6,6,7,7,8,8,8-nonafluorooctyloxy)-pyrimidin-2-yl]-phenol (1.848 g, 4.00 mmol), compound 13 (1.096 g, 4.00 mmol) and triphenylphosphine (1.310 g, 5.00 mmol) in THF (30 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 1.615 g, 2.250 mmol, 58%

Transitions:

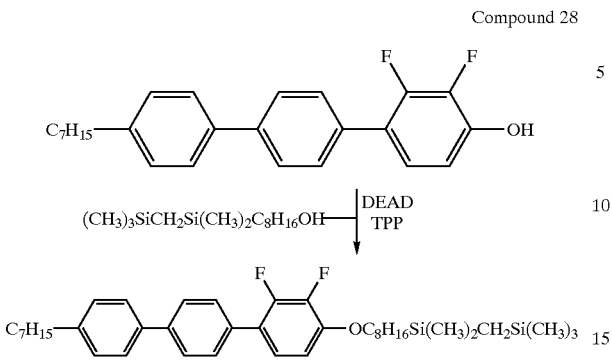
Compound 28

28. 4"-[8-(Dimethyl-trimethylsilanylmethyl-silanyl)-octyloxy]-2",3"-difluoro-4-heptyl-[1,1';4',1"]terphenyl A solution of diethylazodicarboxylate (0.055 g, 0.315 mmol) in THF (5.0 ml) was added dropwise to a stirred solution of 2",3"-difluoro-4-heptyl-[1,1';4',1"]terphenyl-4"-ol (0.095 g, 0.250 mmol), compound 13 (0.0735 g, 0.275 mmol) and triphenylphosphine (0.0825 g, 0.315 mmol) in THF (20 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.022 g, 0.035 mmol, 14%

Transitions:

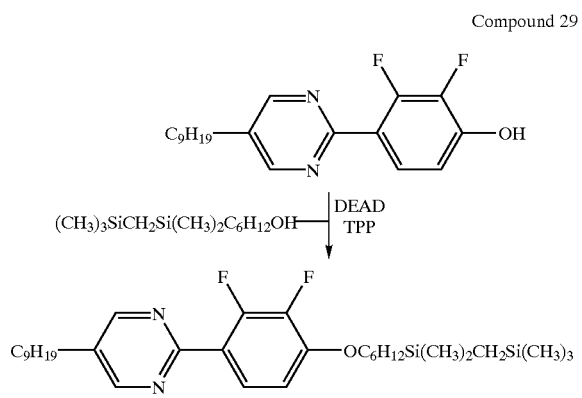
Compound 29

29. 2-{4-[6-(Dimethyl-trimethylsilanylmethyl-silanyl)-hexyloxy]-2,3-difluoro-phenyl}-5-nonyl-pyrimidine A solution of diethylazodicarboxylate (0.087 g, 0.500 mmol) in THF (5.0 ml) was added dropwise to a stirred solution of 2,3-difluoro-4-(5-nonylpyrimidin-2-yl)-phenol (0.134 g, 0.400 mmol), compound 14 (0.108 g, 0.440 mmol) and triphenylphosphine (0.130 g, 0.500 mmol) in THF (20 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.053 g, 0.091 mmol, 24%

Transitions:

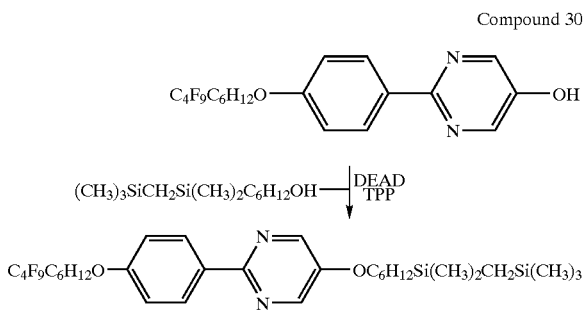
Compound 30

30. 2-{4-[8-(Dimethyl-trimethylsilanylmethyl-silanyl)-hexyloxy]-phenyl}-5-(7,7,8,8,9,9,10,10,10-nonafluorodecyloxy)-pyrimidine A solution of diethylazodicarboxylate (0.0435 g, 0.250 mmol) in THF (5.0 ml) was added dropwise to a stirred solution of 4-[5-(7,7,8,8,9,9,10,10,10-nonafluorodecyloxy)-pyrimidin-2-yl]-phenol (0.098 g, 0.200 mmol), compound 14 (0.049 g, 0.200 mmol) and triphenylphosphine (0.0655 g, 0.250 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.112 g, 0.156 mmol, 78%

Transitions:

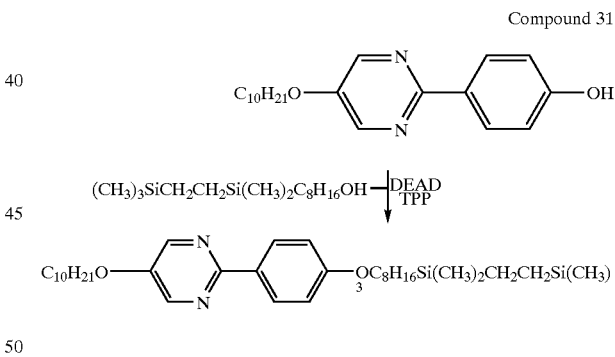
Compound 31

31. 5-Decyloxy-2-{4-[6-(dimethyl-trimethylsilanylethyl-silanyl)-octoxy]-phenyl}-pyrimidine A solution of diethylazodicarboxylate (0.0650 0.375 mmol) in THF (5.0 ml) was added dropwise to a stirred solution of 4-(5-deyloxypyrimidin-2-yl)-phenol (0.0984g, 0.30 mmol), compound 17 (0.083 g, 0.30 mmol) and triphenylphosphine (0.098, 0.375 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.108 g, 0.184 mmol, 61%

Transitions:

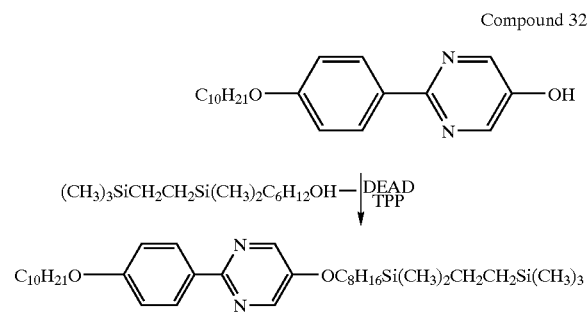

Compound 32

32. 2-(4-Decyloxy-phenyl)-5-{8-[dimethyl-(2-trimethylsilanyl-ethyl)-silanyl]-octyloxy}-pyrimidine A solution of diethylazodicarboxylate (0.065 g, 0.375 mmol) in THF (5.0 ml) was added dropwise to a stirred solution of 2-(4-decyloxyphenyl)-pyrimidin-5-ol (0.0984 g, 0.30 mmol), compound 17 (0.083, 0.30 mmol) and triphenylphosphine (0.098 g, 0.375 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.102 g, 0.173 mmol, 58%

Transitions:

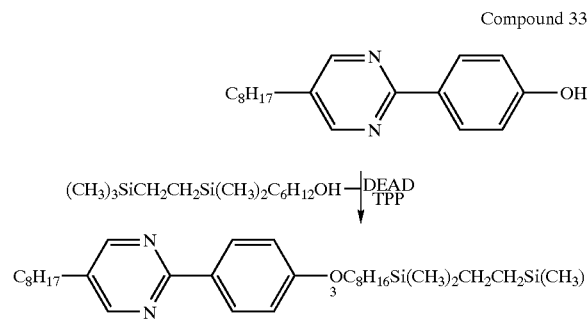

Compound 33

33. 2-(4-{8-[Dimethyl-(2-trimethylsilanyl-ethyl)-silanyl]-octyloxy}-phenyl)-5-octyl-pyrimidine A solution of diethylazodicarboxylate (0.065 g, 0.375 mmol) in THF (5.0 ml) was added dropwise to a stirred solution of 4-(5-octylpyrimidin-2-yl)-phenol (0.085g, 0.300 mmol), compound 17 (0.083 g, 0.300 mmol) and triphenylphosphine (0.098 g, 0.375 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.122 g, 0.224 mmol, 75%

Transitions:

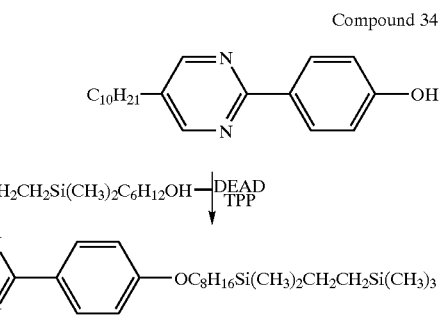

Compound 34

34. 5-Decyl-2-(4-{8-[dimethyl-(2-trimethylsilanyl-ethyl)-silanyl]-octyloxy}-phenyl)-pyrimidine A solution of diethylazodicarboxylate (0.065 g, 0.375 mmol) in THF (5.0 ml) was added dropwise to a stirred solution of 4-(5-decylpyrimidin-2-yl)-phenol (0.094 g, 0.300 mmol), compound 17 (0.083 g, 0.300 mmol) and triphenylphosphine (0.098 g, 0.375 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.112 g, 0.196 mmol, 65%

Transitions:

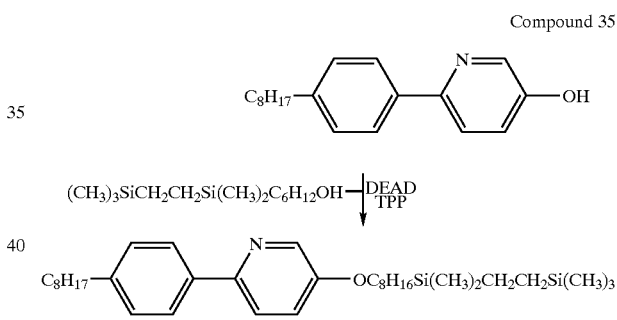

Compound 35

35. 5-{8-[Dimethyl-(2-trimethylsilanyl-ethyl)-silanyl]-octyloxy}-2-(4-octyl-phenyl)-pyridine A solution of diethylazodicarboxylate (0.065 g, 0.375 mmol) in THF (5.0 ml) was added dropwise to a stirred solution of 6-(4-octylphenyl)-pyridin-3-ol (0.085g, 0.300 mmol), compound 17 (0.083 g, 0.300 mmol) and triphenylphosphine (0.098 g, 0.375 mmol) in THF (10 ml). The treaction mixture was stirred at room temperature for 24 h, the solvent removed in vacuo and the residues purified by column chromatography [silica gel eluted with hexane/ethyl acetate (9:1)] to yield a colorless solid that was recrystallized from acetonitrile.

Yield: 0.102 g, 0.188 mmol, 63%

Transitions:

Those of ordinary skill in the art will appreciate that compounds, mixtures, methods of synthesis or purification and method of assessing properties of compounds and mixtures other than those specifically described herein can be applied to the practice of this invention. All art known equivalents of the compounds, mixtures and methods specifically described herein are encompassed by this invention. All references cited herein are incorporated in their entirety by reference herein. Scheme 1

SCHEME 1
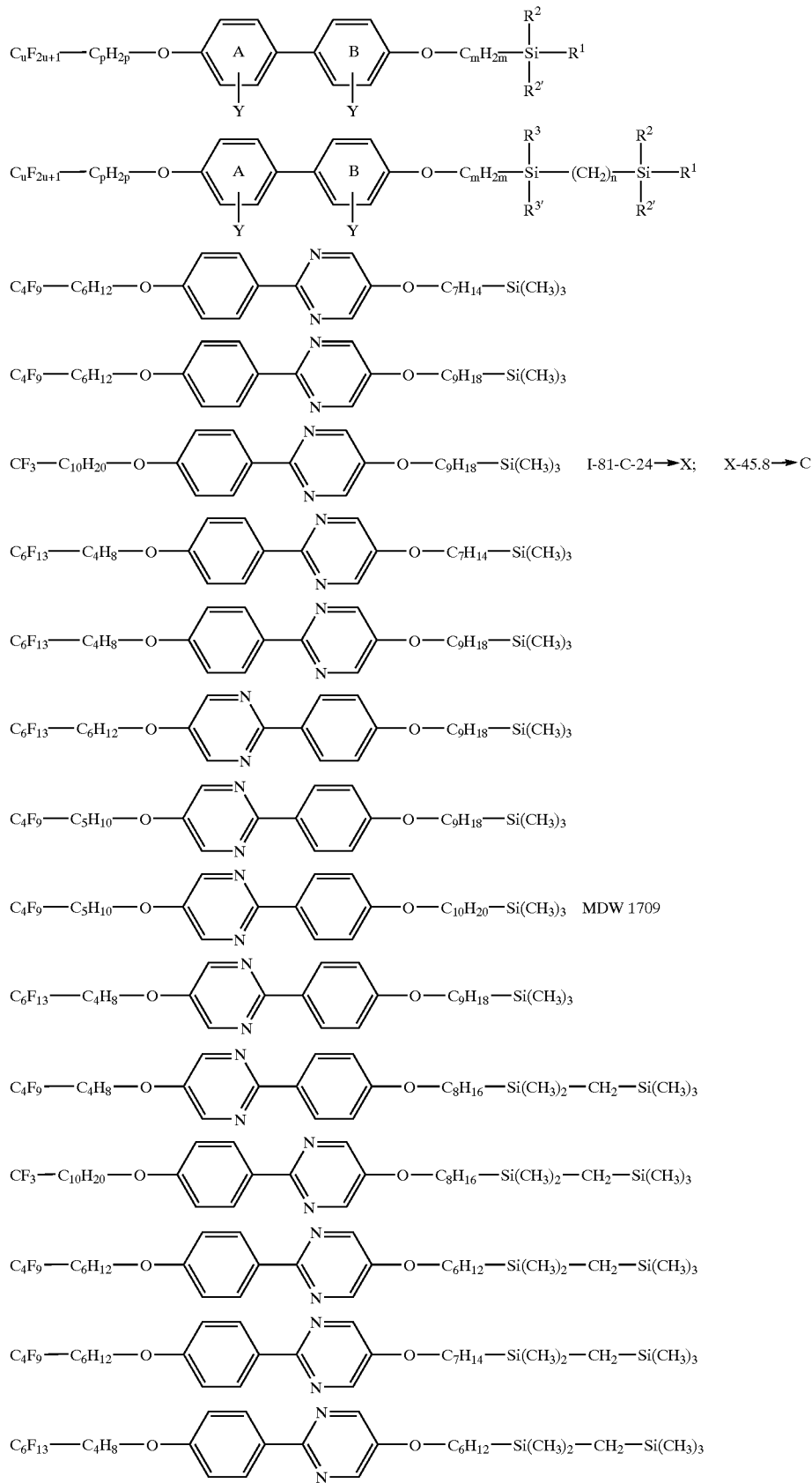

-continued
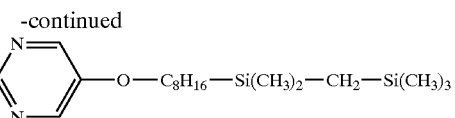
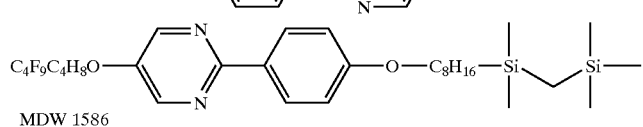
MDW 1586
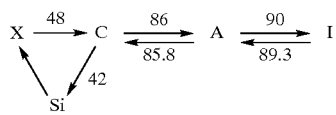
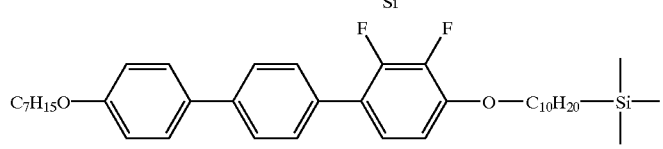
MDW 1701
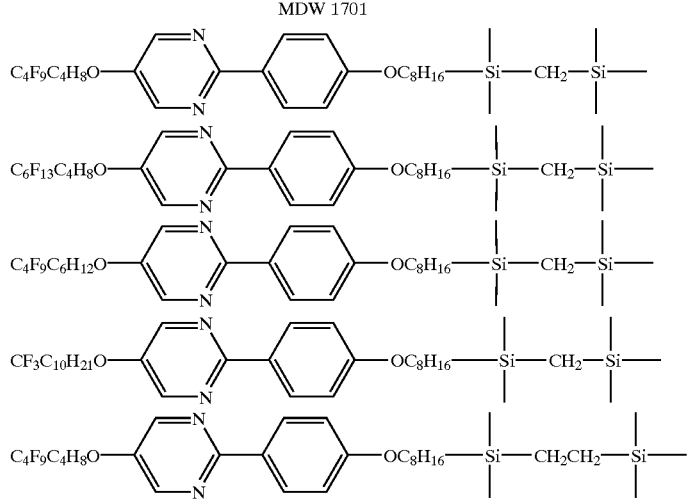
SCHEME 2
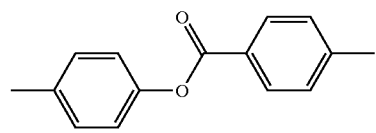
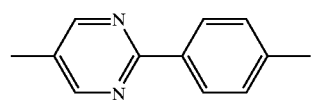
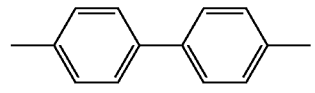
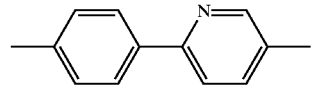
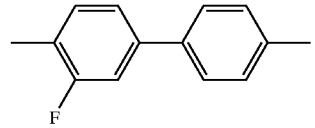
-continued
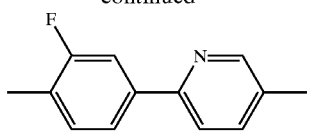
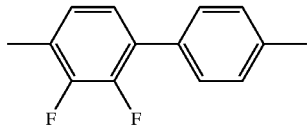
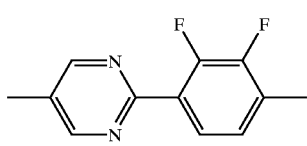
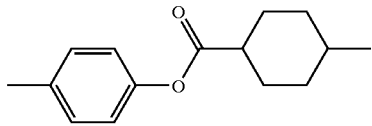

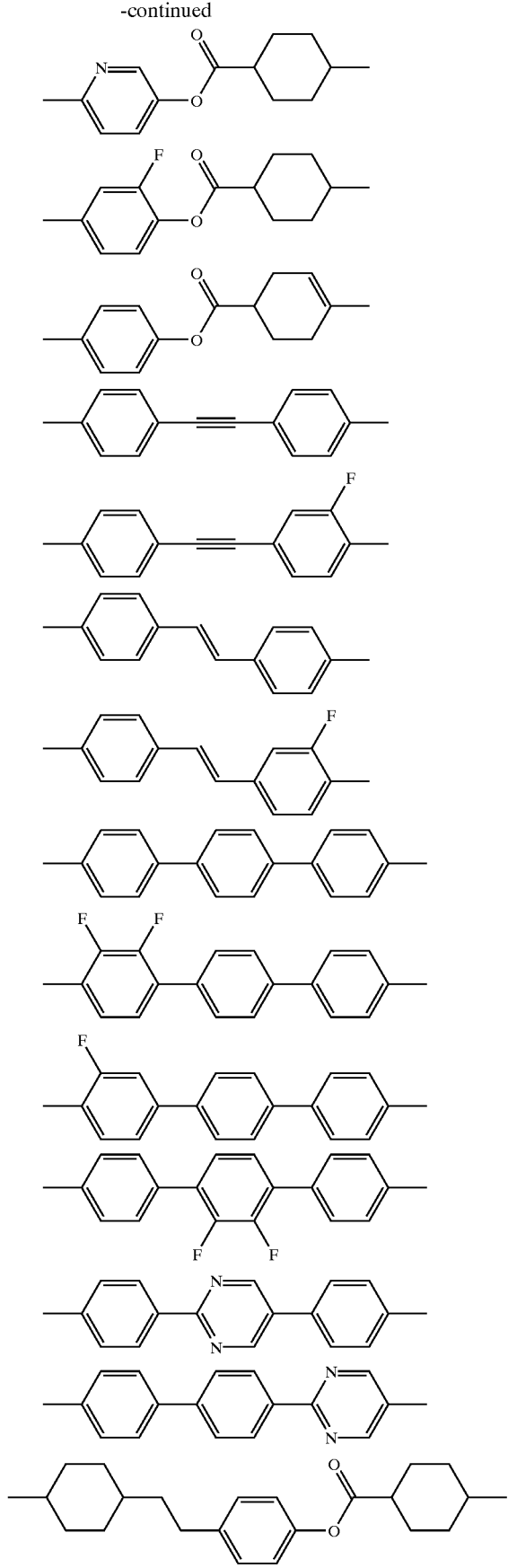
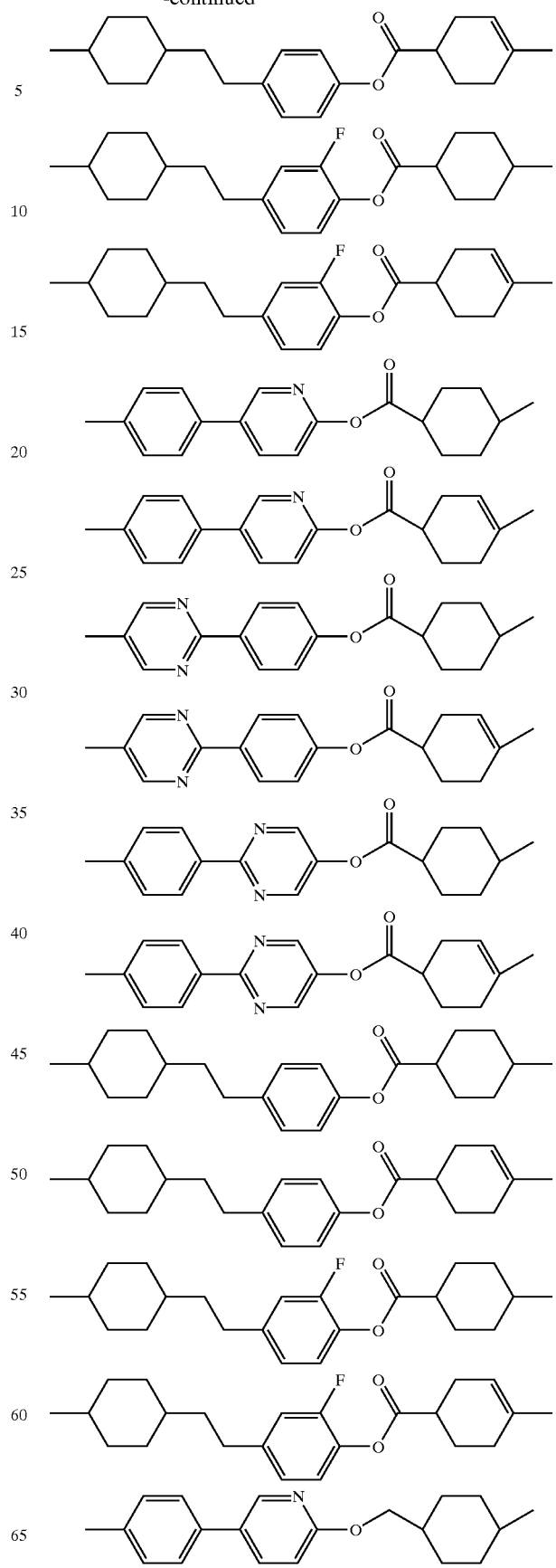

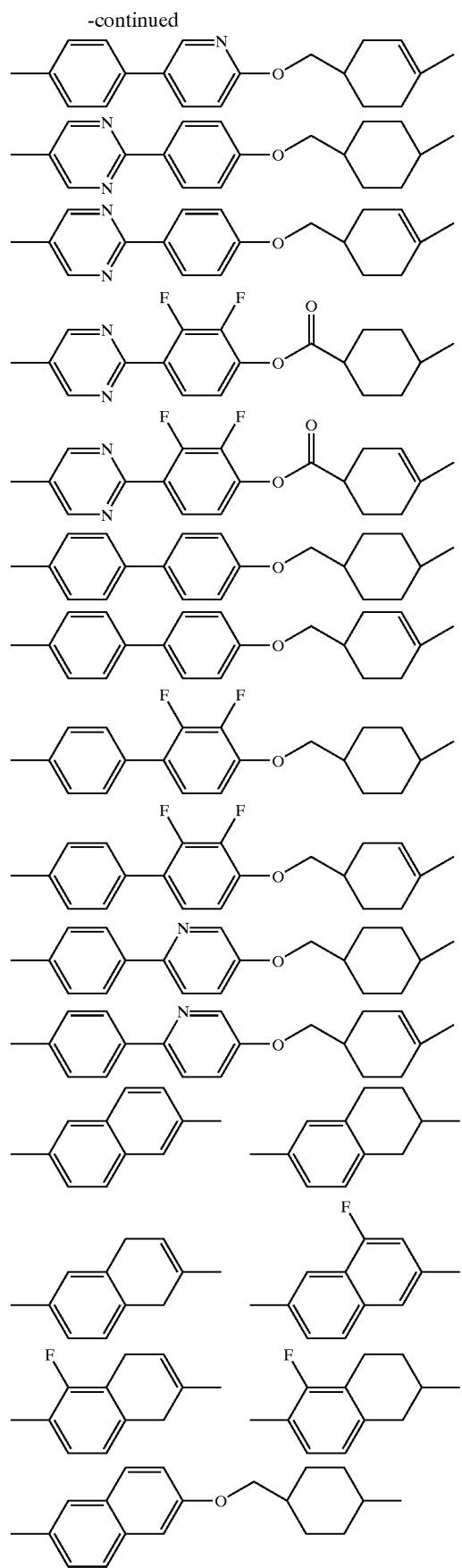
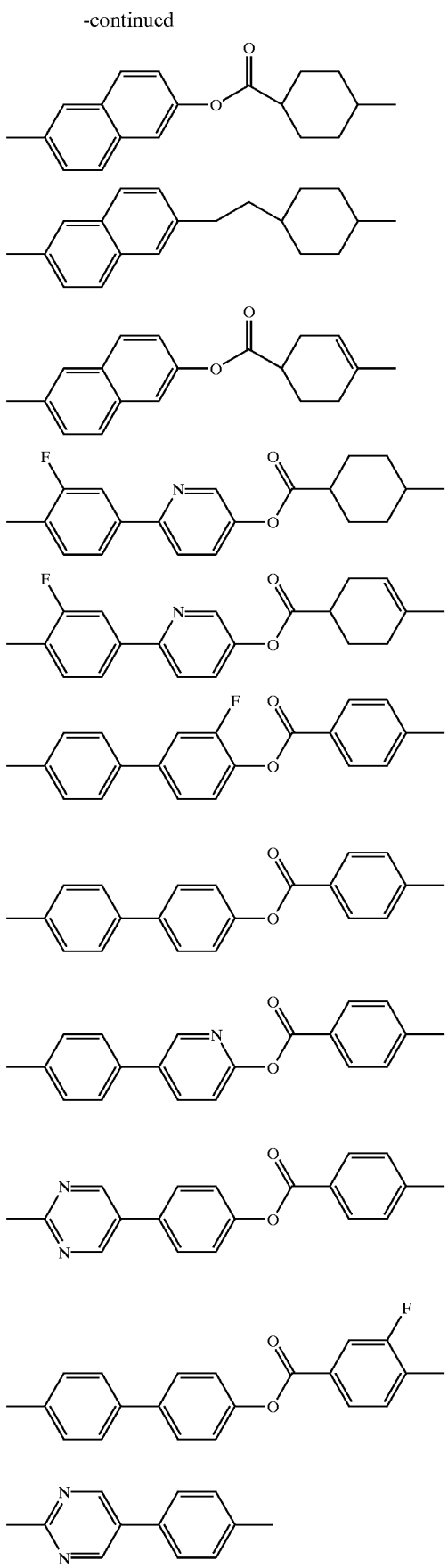

41
-continued

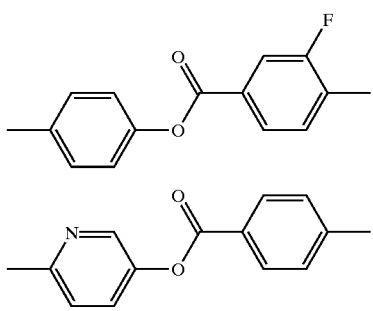

42
-continued

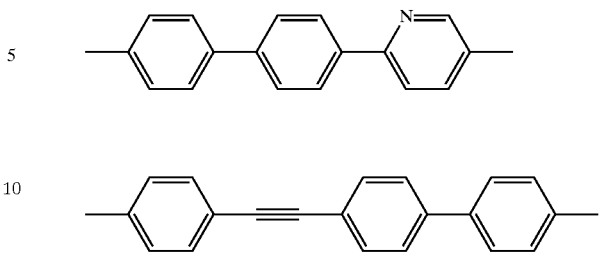

5

10

SCHEME 3

| MDW # | Structure | Phase Diagram |
|---|---|---|
| 950 | C₈H₁₇—⟨Ph⟩—⟨Py(N)⟩—O—CH₂—C*HF—C*HF—C₄H₉ | X <–90 – I – 94–> |
| 987 | C₄H₉C₄H₈O—⟨Pym⟩—⟨Ph⟩—O—CH₂—C(CH₃)(F)—C₄H₉ | X <---21 --- SmC* <–54– SmA <–63–I–53–> S? –57–> |
| 644 | C₁₀H₂₁O—⟨Ph⟩—⟨Pym⟩—O—CH₂CH₂—C*H(CH₃)—CH₂CH₂—CH(CH₃)₂ | X <–20– N <–41– I –43–> –47–> |
| 699 | C₁₀H₂₁O—⟨Ph⟩—⟨Pym⟩—O—CH₂CH₂—C*H(CH₃)—CH₂CH₂—CH(CH₃)₂ | |
| 139 | C₄F₉C₄H₈O—⟨Pym⟩—⟨Ph⟩—O—C(=O)—epoxide—C₃H₇ | X – 75–> I <–86– |
| 337 | C₁₀H₂₁—⟨Pym⟩—⟨Ph⟩—O—C(=O)—⟨Cy⟩—C₅H₁₁ | X <–100– C <–105– N <–169–I |
| 1135 | C₈H₁₇O—⟨Ph⟩—⟨Py⟩—O—C(=O)—⟨Cy⟩—CH₂CH₂—CH(CH₃)₂ | X <–73.5 –S?<–85– C <–104 – A<–175– N <–186–I |

-continued
SCHEME 3

| No. | Structure | Phase transitions |
|---|---|---|
| 1638 | C₈H₁₇O–(3-F-phenyl)–(pyridine)–O–C(=O)–(cyclohexyl)–CH₂CH₂CH₂CH(CH₃)₂ | |
| 1458 | C₅H₁₁–(cyclohexyl)–CH₂CH₂–(2-F-phenyl)–O–C(=O)–(cyclohexyl)–CH₂CH₂CH₂CH(CH₃)₂ | |
| 1671 | C₇H₁₅–(2,3-F₂-phenyl)–(phenyl)–(phenyl)–C₅H₁₁ | X –56–> C –106–> A –131–> N –136–> I |
| 1673 | C₇H₁₅–(phenyl)–(2,3-F₂-phenyl)–(phenyl)–C₅H₁₁ | X –37–> N –112–> I  X <–24– C |
| 1674 | C₇H₁₅–(phenyl)–(phenyl)–(2,3-F₂-phenyl)–C₅H₁₁ | X –66–> SI –75–>C –119–> A –135–>N–137–>I |
| 31 | C₇H₁₅–(pyrimidine)–(phenyl)–OC₇H₁₅ | |
| 3 | C₇H₁₅–(pyrimidine)–(phenyl)–OC₈H₁₇ | X –49–> A –44–>N –69.5–> I |
| 1695 | C₈H₁₇–(pyrimidine)–(phenyl)–OC₆H₁₃ | |
| 5 | C₈H₁₇–(pyrimidine)–(phenyl)–OC₁₂H₂₅ | X –43.2–>C –62.4–>A –66.8–>N–68.2–> I |
| 4 | C₉H₁₉–(pyrimidine)–(phenyl)–OC₈H₁₇ | X –33–>C –60–>A –74.5–> I |
| 913 | C₉H₁₉–(pyrimidine)–(2,3-F₂-phenyl)–OC₇H₁₅ | X –43–>C –50–> I<–44– <–52– |
| 911 | C₉H₁₉–(pyrimidine)–(2,3-F₂-phenyl)–OC₉H₁₉ | X –44–>C –52–> I<–37– <–52– |

-continued
SCHEME 3
374 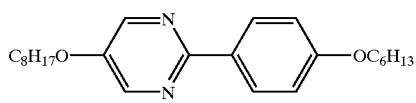
1054 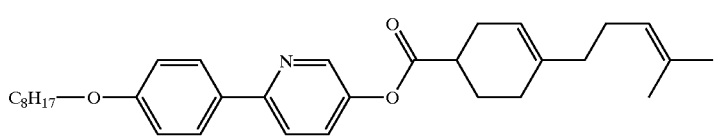   X <--C <--135- N<--150- I-
55-> Sx --82-->
942 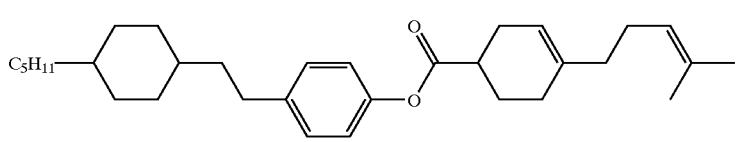
576 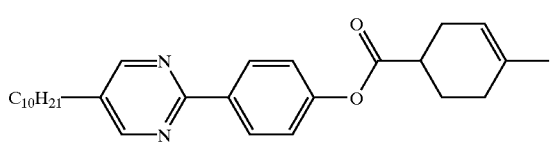   X >--35- S? <--45 - C <--68- N<--107-
I--50-> --54-->
1059 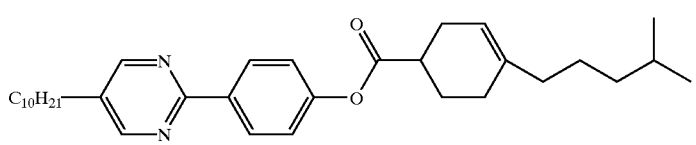
336 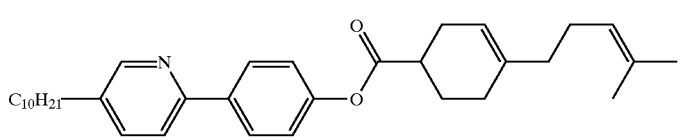   X <--27- C <--83- N<--106- I--40-->
577 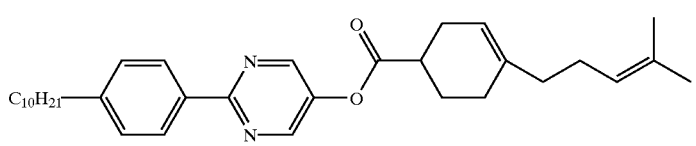
| MDW# | Structure |
|---|---|
| 1701 | 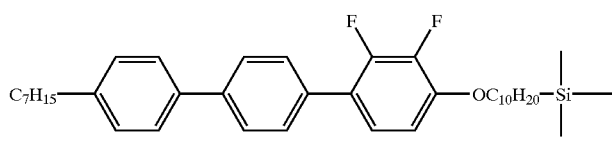 |
| 1658 | 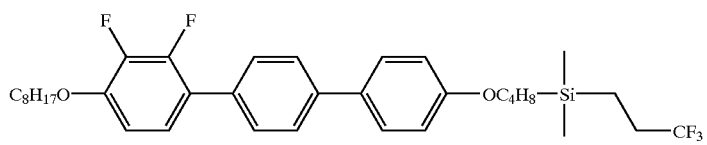 |
| 1592 | 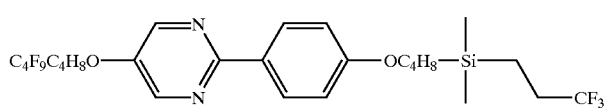 |

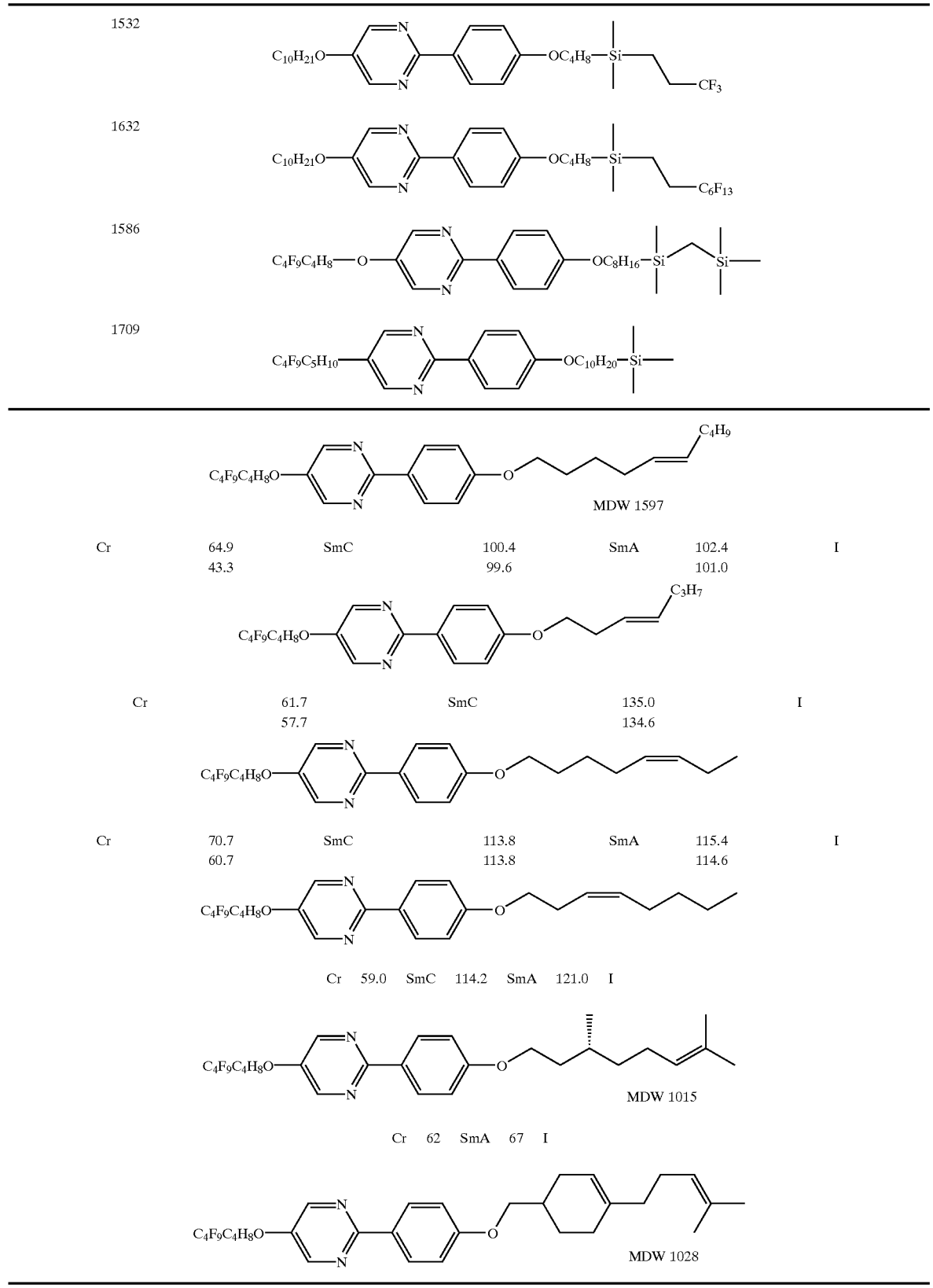

SCHEME 4
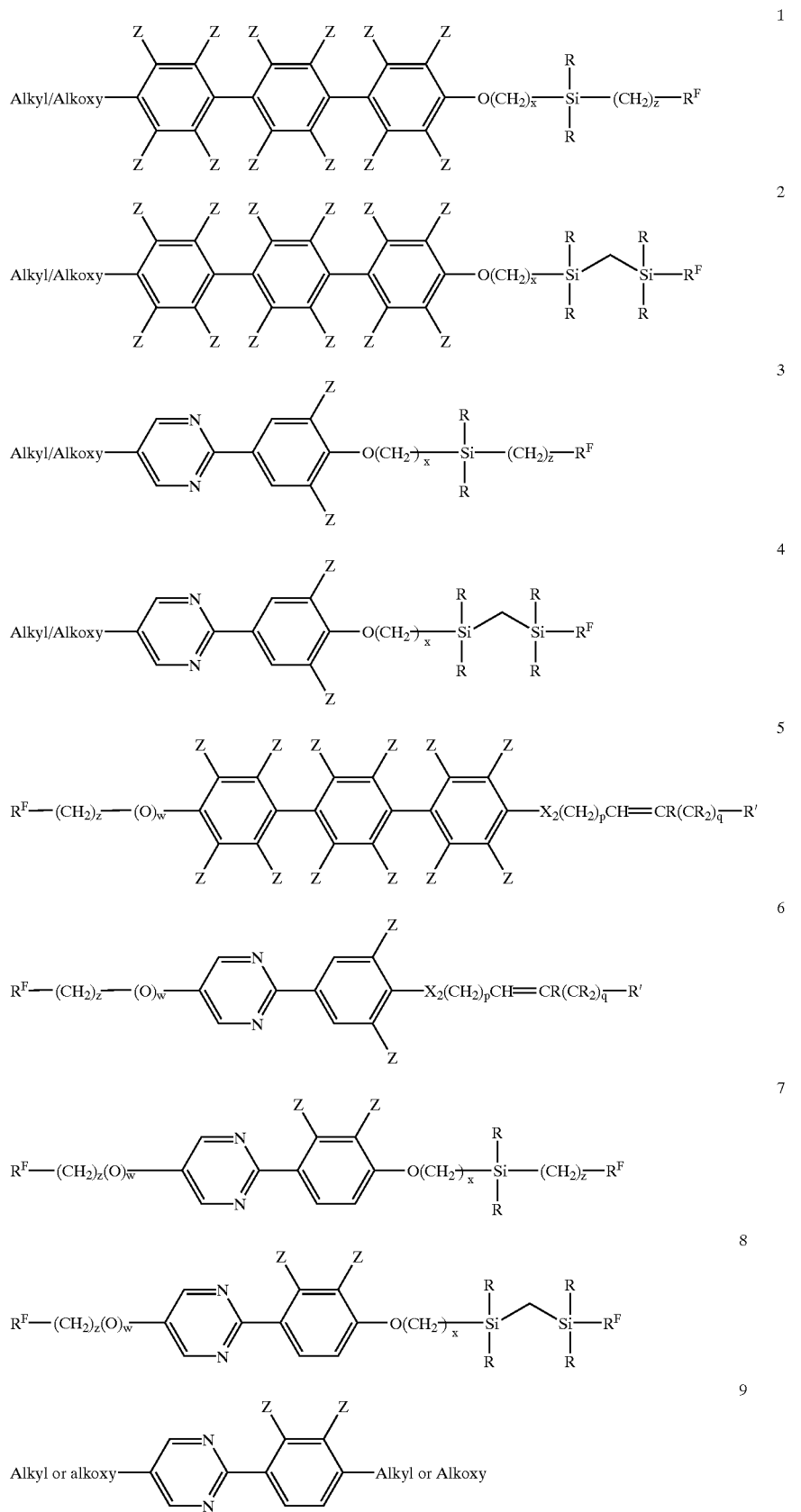

10
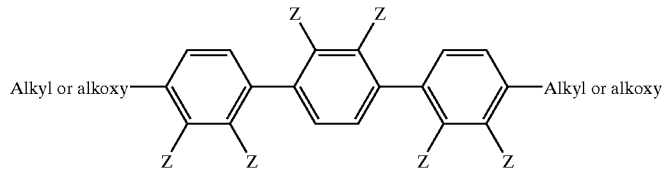
11
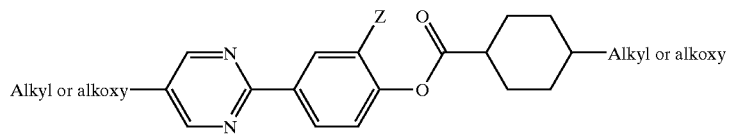
12
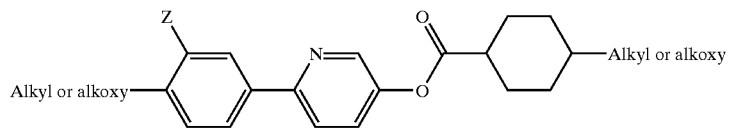
13
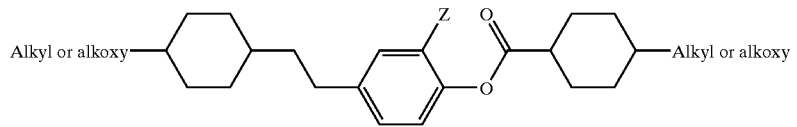
14
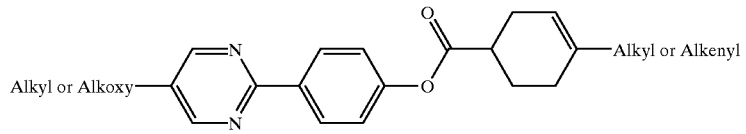
15
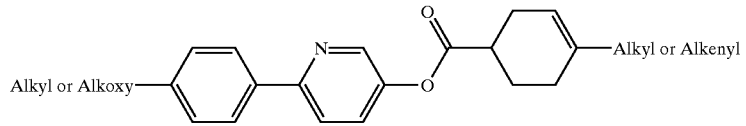
16
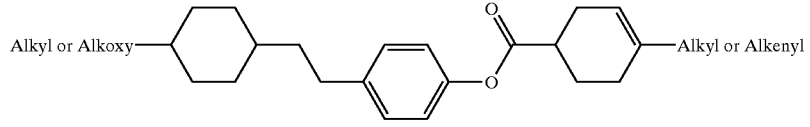
17
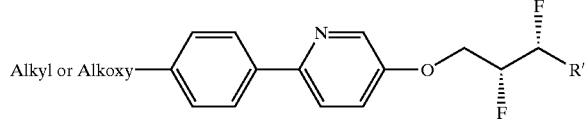
18
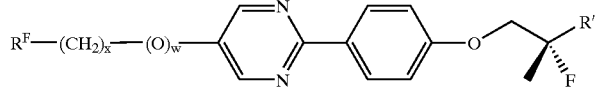

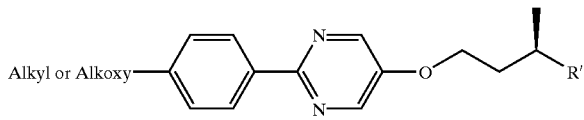

19

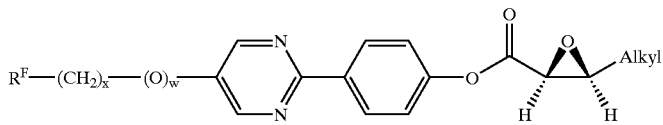

20 wherein p, x and z are integers ranging from 1 to 20, inclusive, q is 0 or an integer ranging from 1 to 20, inclusive; w is 0 or 1; R are alkyl groups, preferably having from 1 to 6 carbon atoms; R' is an alkyl group having from 5 to 20 carbon atoms; $R^F$ is a perfluoroalkyl group; Z is H or a F; and alkyl or alkoxy groups are those that have 5 to 20 carbon atoms.

TABLE 1

| MX # | APT data | | | | | | Phase Info | | |
|------|----|------|--------|-------------|-------|---------|-------------------------------------|--------|--------|
|      | Ps | Visc | E rise | Resistivity | Diele | Applied | Phase diagram | DSC MP | DSC FP |
| 9272 | 26.6 | 83.6  | 127 | 1.6 e+11 | 4.26 | 6 | I – 102.5 – N – 95.9 – A – 85.7 – C | –38.5 | –43 |
| 9295 | 24   | 73    | 130 |          |      |   | I – 102.2 – N – 96.8 – A – 82.8 – C | –30.5 < –25 | |
| 9387 | 36.4 | 171   | 120 | 1.4 e+11 | 4.98 | 6 | I – 99.5 – N – 92 – A – 85 – C – –60 –X | –60 | –60 |
| 9390 | 29.6 | 92.2  | 117 | 2.7 e+11 | 5.16 | 6 | I – 113.8 – N – 111.4 – A – 87.1 – C – 2.1 – Sx | –60 | –60 |
| 9405 | 14.4 | 70.9  | 207 | 3.1 e+11 | 3.92 | 6 | I – 103.8 – N – 100.1 – A – 85.1 – C | –43.1 | –60 |
| 9426 | 29.4 | 195.7 | 145 | 9.5 e+10 | 4.37 | 6 | I – 104.2 – N – 102.3 – A – 90.2 – C | –35.7 | –60 |
| 9431 | 14.2 | 80.3  | 227 | 5 e+11   | 3.98 | 6 | I – 104.4 – N – 96.9 – A – 82.7 – C | –36.3 | –33.8 |

TABLE 2
MX 9212
| Component | Percent | Structure | Phase diagram |
|---|---|---|---|
| 1658 | 3.00 | 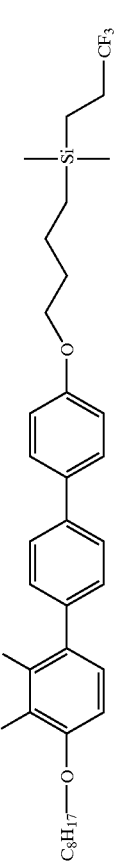 | I 128.4 -> C - 37.5 -> X; X - 41 -> C |
| 1586 | 3.00 | 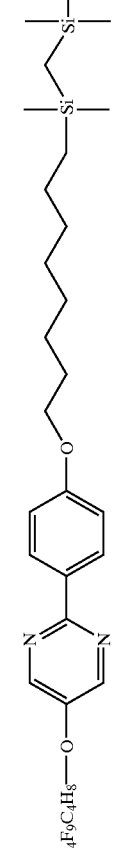 | X - 48 -> C - 86 -> A - 90 -> I; C - 42 -> SI - 25 -> X |
| 1458 | 12.00 | 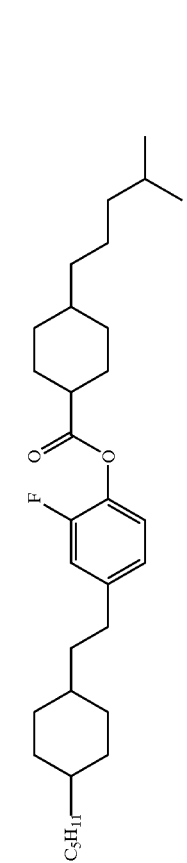 | |
| 1135 | 12.00 | 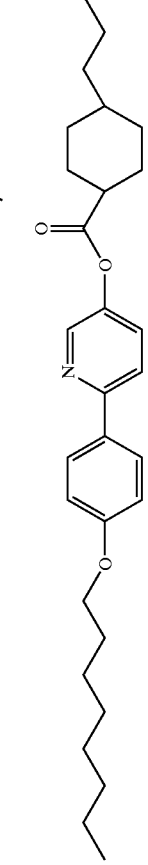 | I - 186 -> N - 175 -> A - 104 -> C - 85 -> S? - -> X; S? <- 73.5 - X |
| 987 | 16.00 | 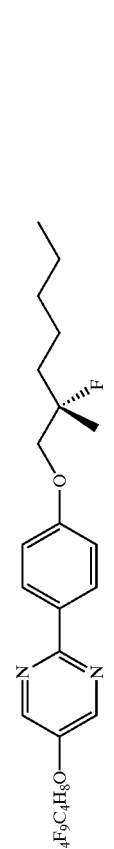 | I - 63 -> A - 54 -> C* - 21 -> X; X - 53 -> S? - 57 -> C* |
| 950 | 2.00 | 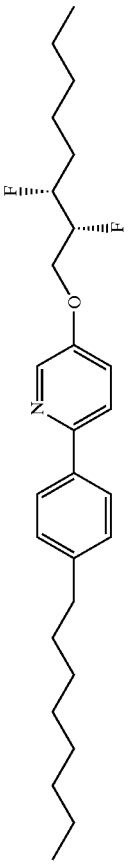 | I - 90 -> X; X - 94 -> I |

TABLE 2-continued

MX 9212

| Component | Percent | Structure | Phase diagram |
|---|---|---|---|
| 913 | 4.00 | 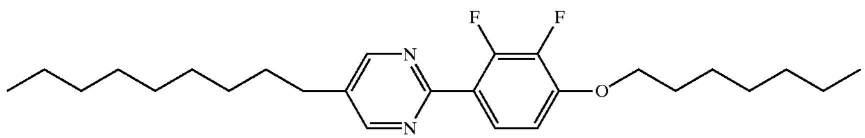 | I - 50 -> C - 32 -> X; X - 43 -> C - 50 -> I |
| 974 | 8.00 | 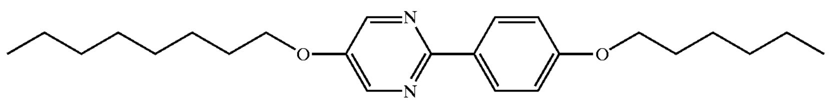 | X - 169 -> N - 105 -> C - 100 -> X; |
| 337 | 15.00 | 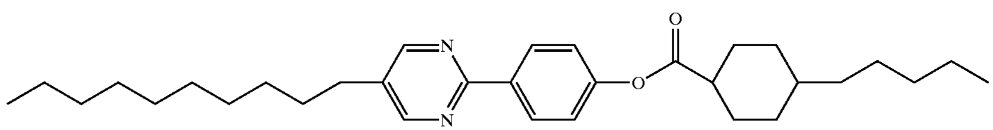 | X - 59.5 - C - 57.5 - A - 63 - N - 71 - I; |
| 006 | 8.33 | 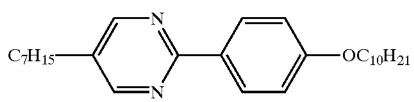 | X - 43.2 - C - 62.4 - A - 66.8 - N - 68.2 - I; |
| 005 | 8.33 | 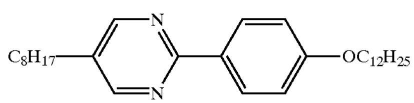 | X - 33 - C - 60 - A - 74.5 - I; |
| 004 | 8.34 | 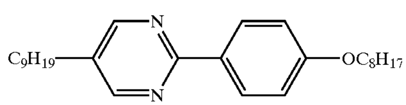 | |

TABLE 3

MX 9245

| Component | w/w Percent | Structure | Phase diagram |
|---|---|---|---|
| 950 | 2.00 | (structure) | I - 90 -> X; X - 94 -> I |
| 987 | 16.00 | (structure) | I - 63 -> A - 54 -> C* - 21 -> X; X - 53 -> S? - 57 -> C* |
| 974 | 8.00 | (structure) | I - 50 -> C - 32 -> X; X - 43 -> C - 50 -> I |
| 913 | 4.00 | (structure) | X 41.1 C 86.1 A 101.3 I 99.6 A 84.8 C |
| 1632 | 3.00 | (structure) | X - 48 -> C - 86 -> A - 90 -> I; C - 42 -> SI - 25 -> X |
| 1586 | 3.00 | (structure) | |
| 337 | 18.00 | (structure) | I - 169 -> N - 105 -> C - 100 -> X; |

TABLE 3-continued
MX 9245
| Component | w/w Percent | Structure | Phase diagram |
|---|---|---|---|
| 1135 | 8.00 | 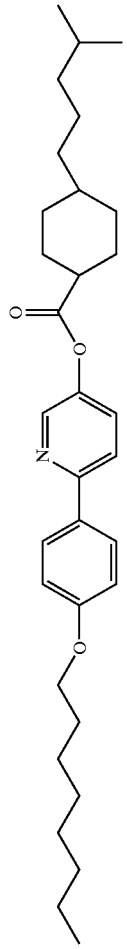 | I - 186 -> N - 175 -> A - 104 -> C - 85 -><br>S? --> X;<br>S? <- 73.5 - X |
| 1598 | 4.00 | 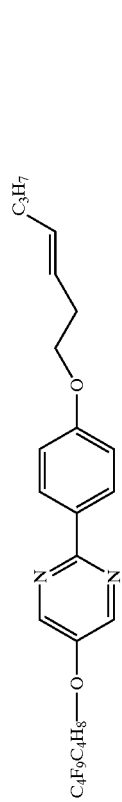 | |
| 1673 | 3.00 | 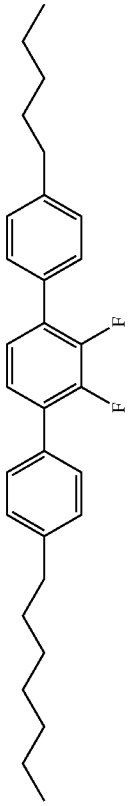 | X - 37 -> N - 112 -> I; C - 24 -> X |
| 1458 | 10.00 | 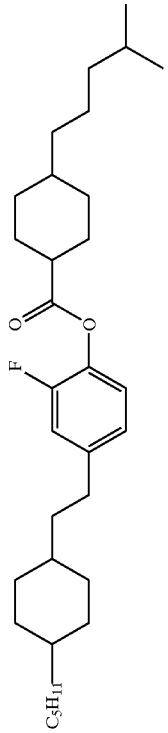 | |
| 3 | 7.00 | 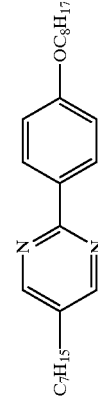 | X - 49 - A - 44 - N - 69.5 - I; |
| 4 | 7.00 | 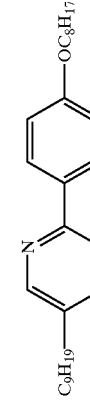 | X - 33 - C - 60 - A - 74.5 - I; |
| 5 | 7.00 | 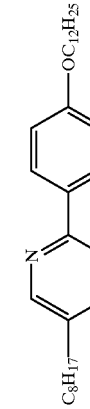 | X - 43.2 - C 62.4 A - 66.8 - N - 68.2 - I; |

TABLE 4

MX 9387

| Component | Percent | Structure | Phase diagram |
|---|---|---|---|
| MDW 950 | 3.00 | 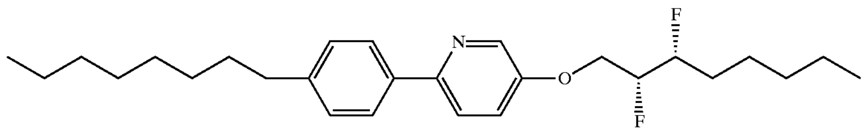 | I - 90 -> X; X - 94 -> I |
| MDW 44 | 1.00 | 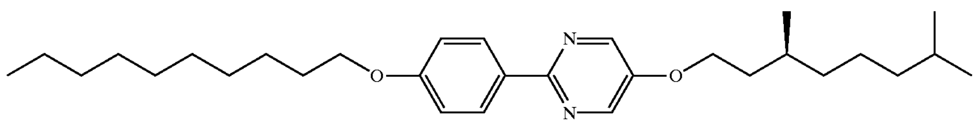 | I - 41 -> N - 20 -> X; X - 43 -> N - 47 -> I |
| MDW 987 | 17.00 | 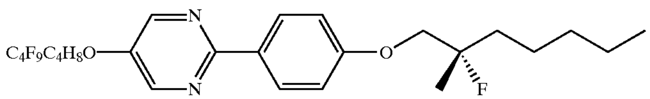 | I - 63 -> A - 54 -> C* - 21 -> X; X - 53 -> S? - 57 -> C* |
| MDW 1054 | 10.00 | 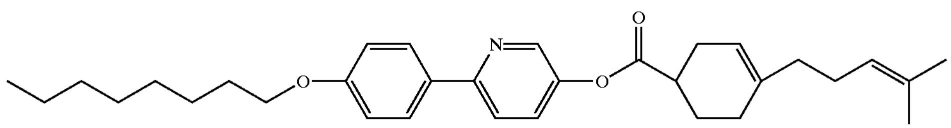 | I - 150 -> N - 135 -> C - -> X; X - 55 -> S? - 82 -> C |
| MDW 1458 | 15.00 | 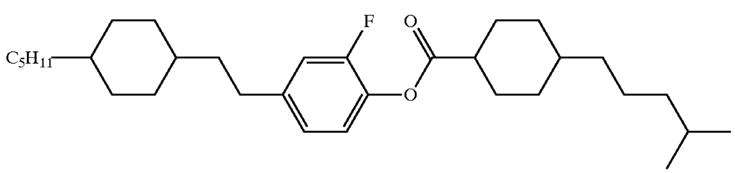 | |
| MDW 336 | 15.00 | 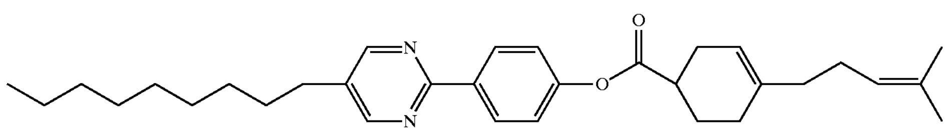 | I - 106 -> N - 83 -> C - 27 -> X; X - 40 -> C |

TABLE 4-continued
MX 9387
| Component | Percent | Structure | Phase diagram |
|---|---|---|---|
| MDW 76 | 12.00 | 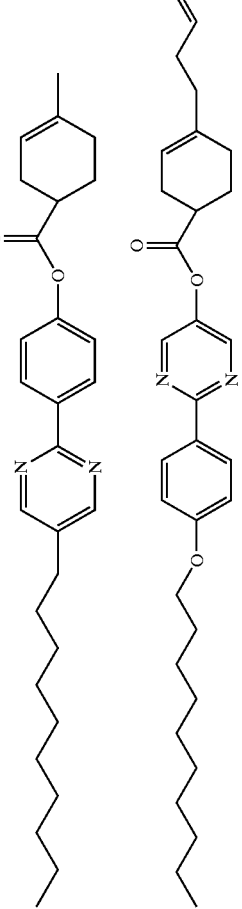 | I - 107 -> N - 68 -> C - 45 -> S? - 35 -> X; X - 50 -> S? - 54 -> C |
| MDW 77 | 3.00 | 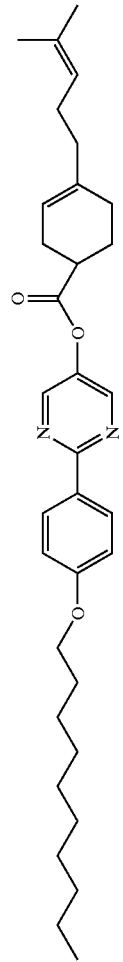 | I - 142 -> N - 121 -> A - 117 -> C - 45 -> S?·; |
| MDW 319 | 10.00 | 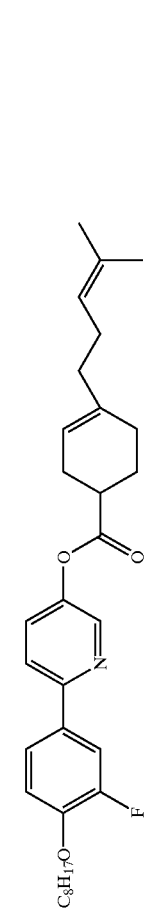 | |
| MDW 913 | 12.00 | 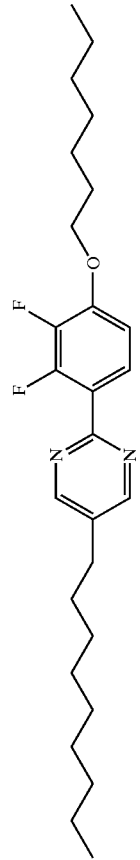 | I - 50 -> C - 32 -> X; X - 43 -> C - 50 -> I |
| MDW 1586 | 3.00 | 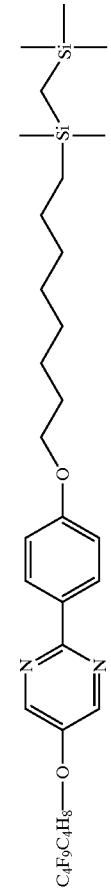 | X - 48 -> C - 86 -> A - 90 -> I; C - 42 -> SI - 25 -> X |

TABLE 5

MX 9390

| Component | Percent | Structure | Phase diagram |
|---|---|---|---|
| 1671 | 15.00 | 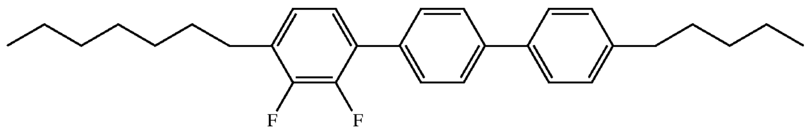 | X - 56 -> C - 106 -> A - 131 -> N - 136 -> I |
| 1674 | 15.00 | 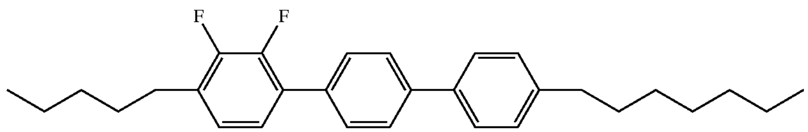 | X - 66 - > Sl - 75 -> C - 119 -> A - 135 -> N - 137 -> I |
| 1673 | 18.00 | 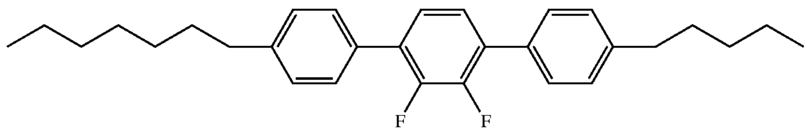 | X - 37 -> N - 112 -> I; C - 24 -> X |
| 1669 | 8.00 | 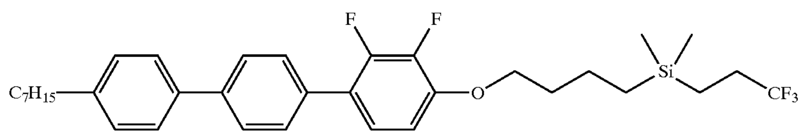 | I - 120.5 -> A - 92.6 -> C - 50 -> Sx - <RT -> X; A - 100 -> I |
| 987 | 18.00 | 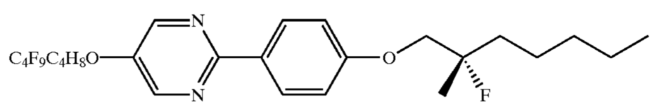 | I - 63 -> A - 54 -> C* - 21 -> X; X - 53 -> S? - 57 -> C* |
| 950 | 2.25 | 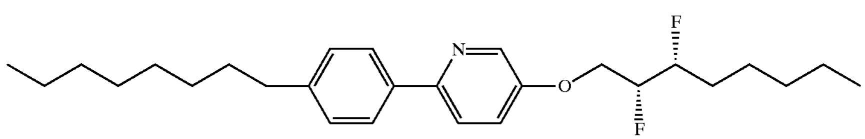 | I - 90 -> X; X - 94 -> I |

TABLE 5-continued
MX 9390
| Component | Percent | Structure | Phase diagram |
|---|---|---|---|
| 337 | 13.75 | 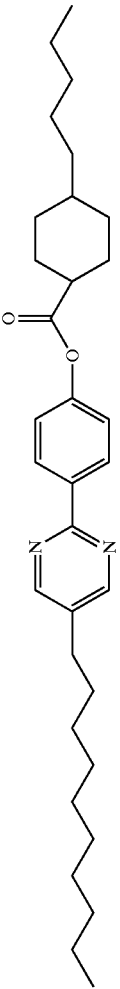 | I - 169 -> N - 105 -> C - 100 - X; |
| 1638 | 5.00 | 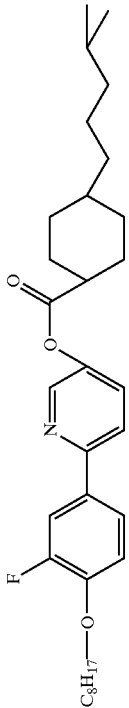 | |
| 1586 | 5.00 | 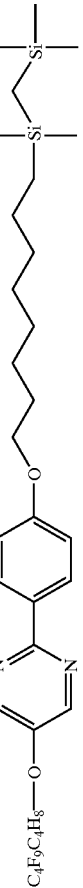 | X - 48 -> C - 86 -> A - 90 -> I; C - 42 -> SI - 25 -> X |

TABLE 6

MX 9405

| Component | Percent | Structure | Phase diagram |
|---|---|---|---|
| 699 | 1.94 | 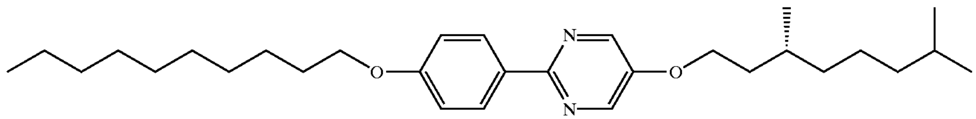 | |
| 987 | 13.81 | 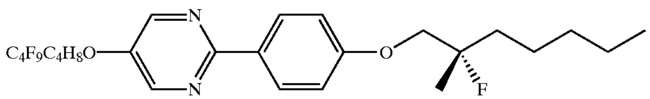 | I - 63 -> A - 54 -> C* - 21 -> X; X - 53 -> S? - 57 -> C* |
| 374 | 10.19 | 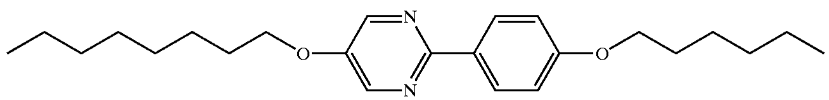 | |
| 1586 | 7.14 | 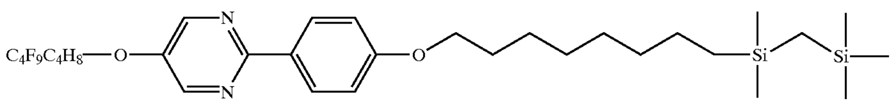 | X - 48 -> C - 86 -> A - 90 -> I; C - 42 -> SI - 25 -> X |
| 337 | 20.11 | 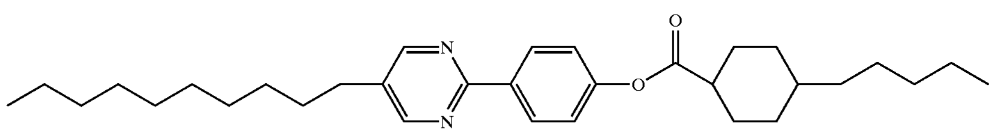 | |
| 1638 | 7.71 | 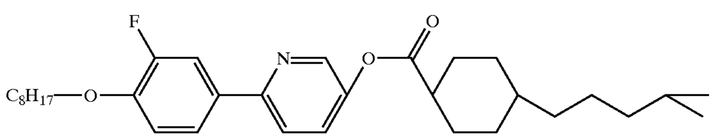 | I - 169 -> N - 105 -> C - 100 -> X. |
| 1598 | 5.96 | 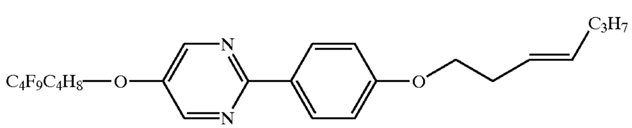 | |

TABLE 6-continued

MX 9405

| Component | Percent | Structure | Phase diagram |
|---|---|---|---|
| 1673 | 2.99 | 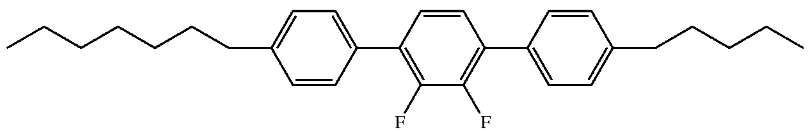 | X - 37 -> N - 112 -> I; C - 24 -> X |
| 1458 | 9.82 | 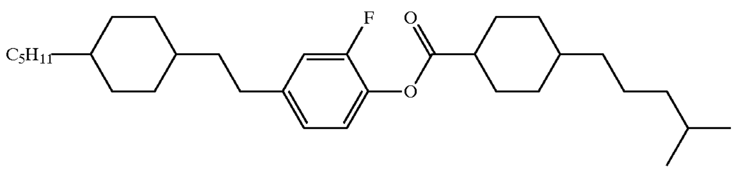 | K - 43.2 - C 62.4 A - 66.8 - N - 68.2 - I; |
| 5 | 13.56 | 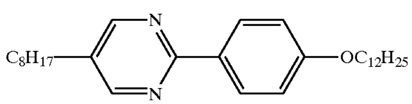 | |
| 1695 | 6.76 | 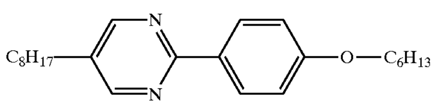 | |
| | 0.00 | | |
| | 0.00 | | |
| | 0.00 | | |
| | 0.00 | | |
| | 0.00 | | |

TABLE 7

MX 9426

| Component | Percent | Structure | Phase diagram |
|---|---|---|---|
| 1598 | 7.17 | (structure) | |
| 987 | 18.25 | (structure) | I - 63 -> A - 54 -> C* - 21 -> X; X - 53 -> S? - 57 -> C* |
| 950 | 2.28 | (structure) | I - 90 -> X; X - 94 -> I |
| 1673 | 7.19 | (structure) | X - 37 -> N - 112 -> I; C - 24 -> X |
| 1671 | 4.08 | (structure) | X - 56 -> C - 106 -> A - 131 -> N - 136 -> I |
| 1674 | 4.13 | (structure) | X - 66 -> SI - 75 -> C - 119 -> A - 135 -> N - 137 -> I |
| 337 | 26.18 | (structure) | I - 169 -> N - 105 -> C - 100 -> X; |

TABLE 7-continued

MX 9426

| Component | Percent | Structure | Phase diagram |
|---|---|---|---|
| 374 | 10.22 | [structure: pyrimidine with hexyloxy and heptyloxyphenyl] | X - 43.2 - C 62.4 A - 66.8 - N - 68.2 - I; |
| 5 | 7.42 | [structure: C$_8$H$_{17}$-phenyl-pyrimidine-phenyl-OC$_{12}$H$_{25}$] | |
| 1586 | 5.93 | [structure: C$_4$F$_9$C$_4$H$_8$-O-pyrimidine-phenyl-O-(CH$_2$)$_n$-Si(CH$_3$)$_2$-CH$_2$-Si(CH$_3$)$_3$] | X - 48 -> C - 86 -> A - 90 -> I; C - 42 -> SI - 25 -> X |
| 1597 | 7.15 | [structure: C$_4$H$_9$C$_4$H$_8$-O-pyrimidine-phenyl-O-(CH$_2$)$_n$-CH=CH-C$_4$H$_9$] | |
| | 0.00 | | |
| | 0.00 | | |
| | 0.00 | | |
| | 0.00 | | |

TABLE 8
MX 9431
| Component | Percent | Structure | Phase diagram |
|---|---|---|---|
| MDW 50 | 1 40 | 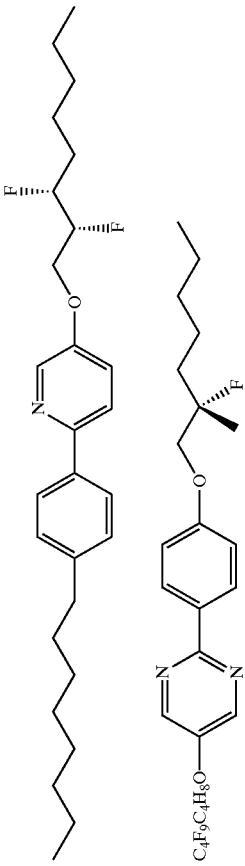 | I - 90 -> X; X - 94 -> I |
| MDW 37 | 11.20 | 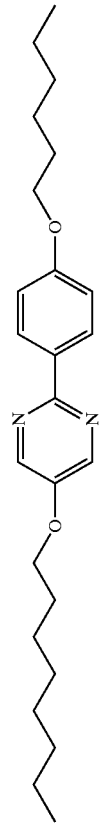 | I - 63 -> A - 54 -> C* - 21 -> X; X - 53 -> S? - 57 -> C* |
| MDW 74 | 10.00 | 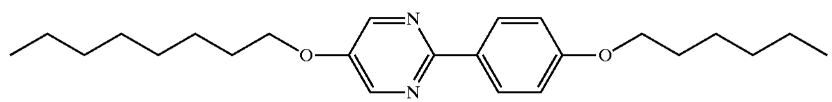 | |
| MDW 1661 | 5.00 | 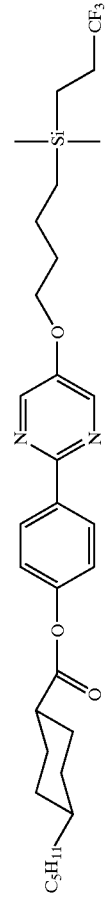 | I - 129.6 -> N - 71 -> Sx1 - 66.5 -> Sx2 - 64 -> X |
| MDW 1586 | 8.00 | 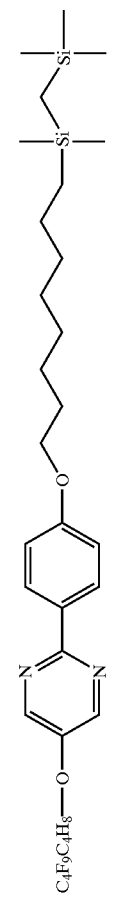 | X - 48 -> C - 86 -> A - 90 -> I; C - 42 -> SI - 25 -> X |
| MDW 1137 | 21.40 | 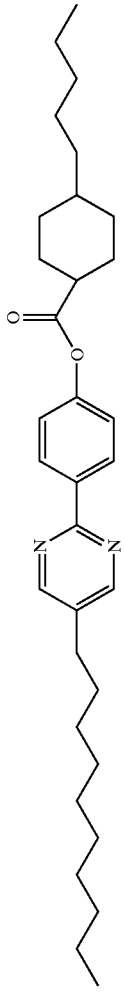 | I - 169 -> N - 105 -> C - 100 -> X; |
| MDW 638 | 8.00 | 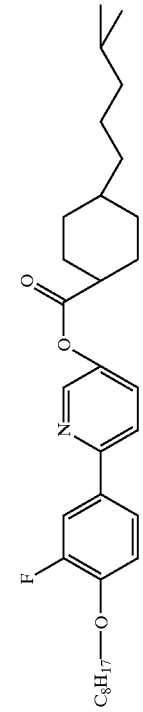 | |

TABLE 8-continued
MX 9431
| Component | Percent | Structure | Phase diagram |
|---|---|---|---|
| MDW 458 | 10.00 | 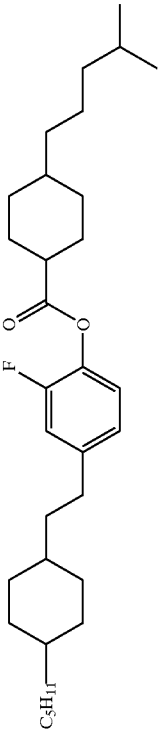 | |
| MDW 695 | 8.50 | 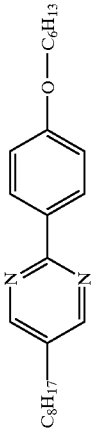 | |
| MDW | 16.50 | 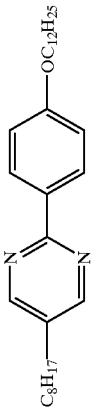 | X - 43.2 - C 62.4 A - 66.8 - N - 68.2 - I; |

TABLE 9

| MX # | | Ps | APT data Visc | E rise | Dielectric | Phase Info Phase diagram | DSC MP | DSC FP |
|---|---|---|---|---|---|---|---|---|
| 9387 | x | 36.4 | 171 | 120 | 4.98 | I – 98.I – N – 91.4 – A – 83.9 – C | −60 | −60 |
| 9533 | | 37 | 128 | 122 | 5.23 | I – 97.2 – N – 88 – A – 82 – C | −41.3 | <−60 |
| 9530 | x | 20.5 | 78 | 97 | 4.96 | I – 113.2 – N – 110.6 – A – 83.2 – C | −11.3 | <−60 |
| 9532 | | 21.2 | 83.4 | 190 | 4.92 | I – 128.3 – N – 81.5 – C – 81.5 | −8 | −17.5 |

TABLE 10

MX number 9533

| Component | Percent | Milligrams | Structure | Total percent 100 |
|---|---|---|---|---|
| 950 | 3.06 | | 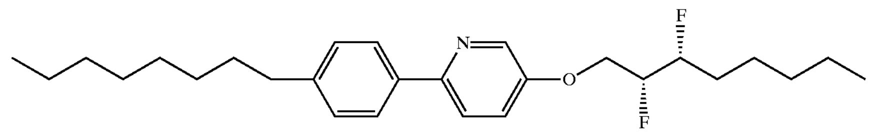 | |
| 644 | 1.02 | | 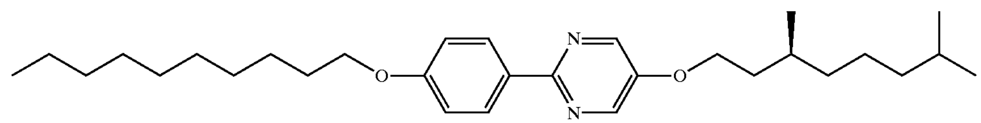 | |
| 987 | 17.35 | | 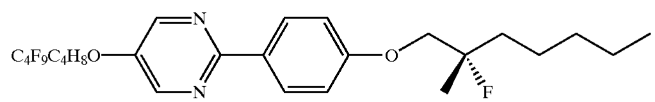 | |
| 1054 | 10.20 | | 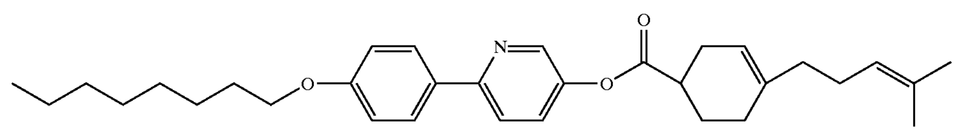 | |
| 1458 | 15.31 | | 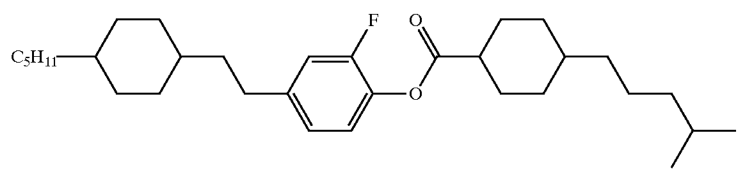 | |
| 336 | 15.31 | | 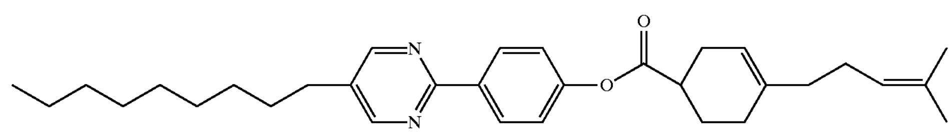 | |

TABLE 10-continued
MX number 9533
| Component | Percent | Milligrams | Structure |
|---|---|---|---|
| 576 | 12.24 | | 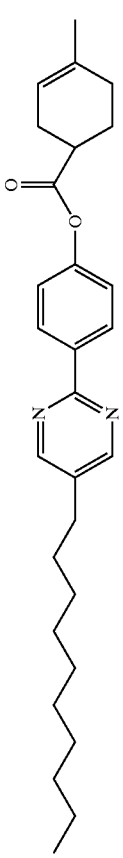 |
| 577 | 3.06 | | 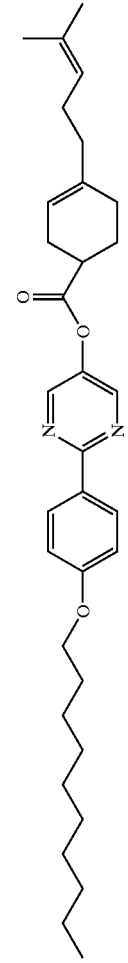 |
| 1319 | 10.20 | | 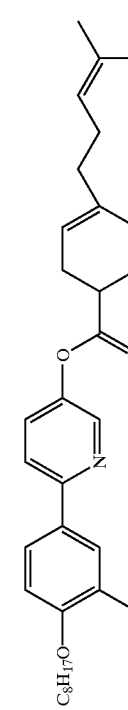 |
| 913 | 12.24 | | 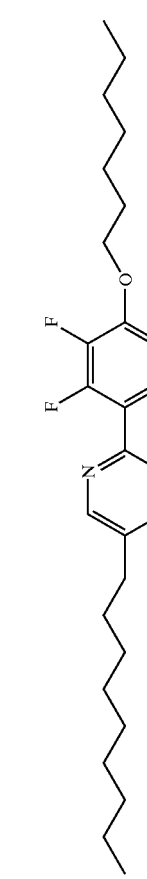 |
Total percent 100

TABLE 11

MX number 9532

| Component | Percent | Structure |
|---|---|---|
| 1671 | 16.67 | 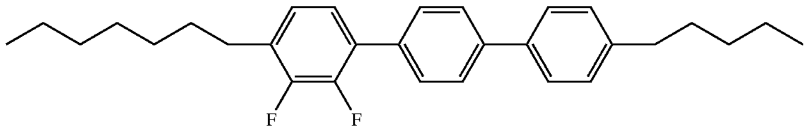 |
| 1674 | 16.67 | 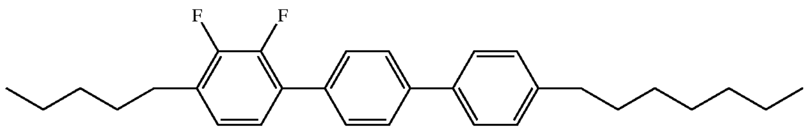 |
| 1673 | 33.33 | 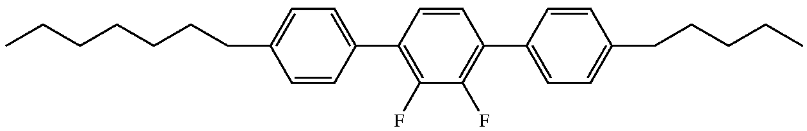 |
| 987 | 17.78 | 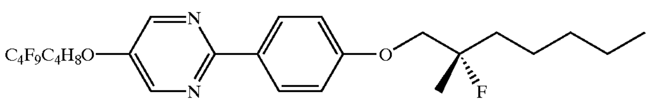 |
| 950 | 2.22 | 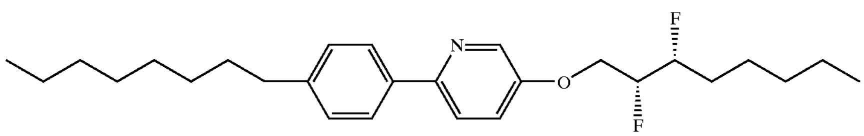 |
| 337 | 13.33 | 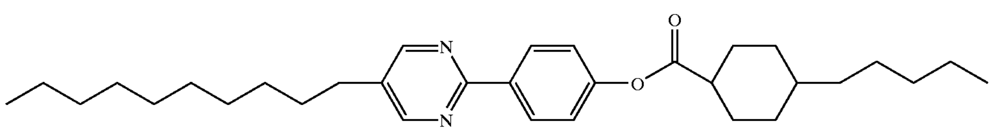 |

We claim:

1. A liquid crystal composition comprising one or more compounds of formula:

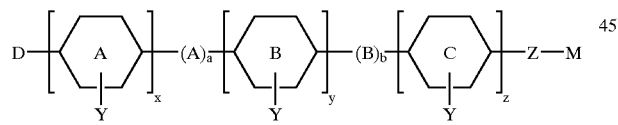

where D is:

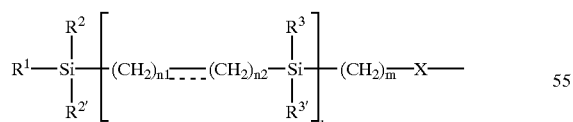

where:
R$^1$ is an alkyl or alkenyl group having j carbon atoms and R$^2$, R$^{2'}$, R$^3$ and R$^{3'}$, independently of one another, are alkyl groups having from 1–6 carbon atoms;
n1 and m are integers from 1 to about 20;
n2 can be zero or an integer from 1 to 20 where the dashed line indicates a possible double or triple bond;
k is 0 or an integer from 1 to 10;
X is oxygen or a single bond; and
j is an integer from 1 to 18; and
wherein a, b, x, y, z can be 0 or 1; x+y+z is 1, 2 or 3, when x is 0, a is 0; when z is 0, b is 0;
A and B, independently, when present, can be —O—, —COO—, —OOC—, —CH$_2$—CH$_2$—, —CH=CH—, —C≡C—, —CH=CH—CH=CH—, —O—CH$_2$— or —CH$_2$—O;
the A, B and C rings, independently of one another, are aromatic rings or alicyclic rings,
where one or two carbons in the A, B or C rings that are aromatic can be replaced with a N, O or S and one or two of the carbons in the A, B or C rings that are alicyclic can be replaced with a N; O or S or a C=O group; provided that the A, B, or C rings are not a 3,4-difluoropyridine ring;
Y can represent up to four substituents on aromatic rings and up to 10 substituents on an alicyclic ring where Y can a halogen, CN group, NO$_2$, alkyl or alkoxy;
Z is a single bond, an —O— or a —COO— or —OOC— group, and
M is a tail group which can be:
a non-fluorinated alkyl, or ether group or R$^F$,
where R$^F$ is an alkyl, or ether group which is fully or partially fluorinated.

2. The LC composition of claim 1 wherein D is:

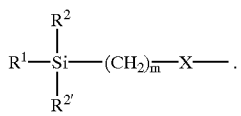

3. The LC composition of claim 2 wherein R1, R2, and R2' are methyl groups and m is an integer ranging from 2 to 20, inclusive.

4. The LC composition of claim 3 wherein X is O.

5. The LC composition of claim 4 wherein M is $R^F$.

6. The LC composition of claim 5 wherein $R^F$ is:

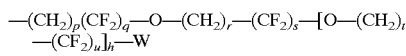

where h is 0 or an integer ranging from 1 to 10, inclusive, p, q, r, s, t, u, v, and w are 0 or integers ranging from 1 to about 20, inclusive and where p+q+r+s+h(t+u) equal to about 20, inclusive.

7. The LC composition of claim 6 wherein $R^F$ is:

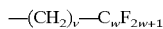

where v and w are integers ranging from 1 to 20, inclusive, and v+w is 5 to 20, inclusive.

8. The LC composition of claim 6 wherein the core is a phenylpyrimidine.

9. The LC composition of claim 6 wherein the core is an optionally substituted terphenyl group.

10. The LC composition of claim 9 wherein the core is substituted with one or two fluorines.

11. A liquid crystal composition comprising one or more compounds of formula;

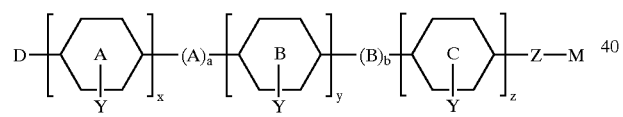

wherein D is:

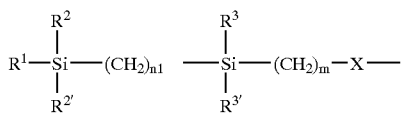

where:

R¹ is an alkyl or alkenyl group having j carbon atoms and R², R²', R³ and R³', independently of one another, are alkyl groups having from 1–6 carbon atoms;

n1 and m are integers from 1 to about 20;

X is oxygen or a single bond; and j is an integer from 1 to 18; and wherein a, b, x, y, z can be 0 or 1; x+y+z is 1, 2 or 3, when x is 0, a is 0; when z is 0, b is 0;

A and B, independently, when present, can be —O—, —COO—, —OOC—, —CH₂—CH₂—, —CH=CH—, —C≡C—, —CH=CH—CH=CH—, —O—CH₂— or —CH₂—O—;

the A, B and C rings, independently of one another, are aromatic rings or alicyclic rings, where one or two carbons in the A, B or C rings that are aromatic can be replaced with a N, O or S and one or two of the carbons in the A, B or C rings that are alicyclic can be replaced with a N, O or S or a C=O group; provided that the A, B or C rings are not a 3,4-difluoropropyridine ring;

Y can represent up to four substituents on aromatic rings and up to 10 substituents on an alicyclic ring where Y can a halogen, CN group, NO₂, alkyl or alkoxy;

Z is a single bond, an —O— or a —COO— or —OOC— group, and

M is a tail group which can be:

a non-fluorinated alkyl, or other group or $R^F$.

where $R^F$ is an alkyl, or ether group which is fully or partially fluorinated.

12. The LC composition of claim 11 wherein R¹, R², R²', R³ and R³' are methyl groups, m is an integer ranging from 2 to 20, inclusive, and n1 is an integer ranging from 1 to 5 inclusive.

13. The LC composition of claim 12 wherein X is O.

14. The LC composition of claim 13 wherein M is $R^F$.

15. The LC composition of claim 14 wherein $R^F$ is:

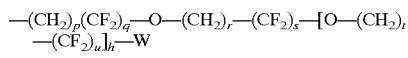

where h is 0 or an integer ranging from 1 to 10, inclusive, p, q, r, s, t, u, v, and w are 0 or integers ranging from 1 to about 20, inclusive and where p+q+r+s+h(t+u) is equal to about 20, inclusive, where W is a hydrogen or fluorine.

16. The LC composition of claim 14 wherein $R^F$ is:

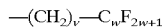

where v and w are integers ranging from 1 to 20, inclusive, and v+w is 5 to 20, inclusive.

17. The LC composition of claim 14 wherein the core is a phenylpyrimidine.

18. The LC composition of claim 14 wherein the core is an optionally substituted terphenyl group.

19. The LC composition of claim 18 wherein the core is substituted with one or two fluorines.

20. The LC composition of claim 1 wherein the core is phenylpyrimidine.

21. The LC composition of claim 1 wherein the core is optionally substituted terphenyl.

22. The LC composition of claim 1 wherein the core is:

[structure showing cyclohexyl-CH2CH2-phenyl-methyl]

or

[structure showing cyclohexyl-CH2CH2-phenyl-pyrimidine]

or

[structure showing cyclohexyl-CH2CH2-phenyl-pyrimidine].

23. The LC composition of claim 22 wherein M is $R^F$.

24. The LC composition of claim 23 wherein D is:

$$R^1-\underset{\underset{R^{2'}}{|}}{\overset{\overset{R^2}{|}}{Si}}-(CH_2)_m-X-\ .$$

25. The LC composition of claim 24 wherein $R^F$ is:

—(CH$_2$)$_v$—C$_w$F$_{2w+1}$ where v and w are integers ranging from 1 to 20, inclusive, and v+w is 5 to 20, inclusive.

26. The LC composition of claim 23 wherein D is:

$$R^1-\underset{\underset{R^{2'}}{|}}{\overset{\overset{R^2}{|}}{Si}}-(CH_2)_{n1}-\underset{\underset{R^{3'}}{|}}{\overset{\overset{R^3}{|}}{Si}}-(CH_2)_{\overline{m}}-X-\ .$$

27. The LC composition of claim 26 wherein $R^F$ is:

—(CH$_2$)$_v$—C$_w$F$_{2w+1}$ where v and w are integers ranging from 1 to 20, inclusive, and v+w is 5 to 20, inclusive.

28. The LC composition of claim 1 which exhibits a smectic C phase.

29. The LC composition of claim 28 which exhibits a smectic A phase.

30. The LC composition of claim 29 which exhibits a nematic phase.

31. The LC composition of claim 1 which has a freezing point less than or equal to −60° C.

32. The LC composition of claim 1 which has a freezing point which is 10° C. or more lower than its melting point.

33. The LC composition of claim 1 further comprising one or more compounds of formula:

Alkyl or alkoxy—[pyrimidine]—[phenyl(Z,Z)]—Alkyl or Alkoxy where Z is H or F.

34. The LC composition of claim 33 further comprising one or more compounds of formula:

Alkyl or alkoxy—[phenyl(Z,Z)]—[phenyl(Z,Z)]—[phenyl(Z,Z)]—Alkyl or alkoxy where Z is H or F.

35. The LC composition of claim 34 further comprising one or more compounds of formulas:

$R^F$—(CH$_2$)$_z$—(O)$_w$—[phenyl(Z,Z)]—[phenyl(Z,Z)]—[phenyl(Z,Z)]—X$_2$(CH$_2$)$_p$CH=CR(CR$_2$)$_{\overline{q}}$R'   or $R^F$—(CH$_2$)$_z$—(O)$_w$—[pyrimidine]—[phenyl(Z,Z)]—X$_2$(CH$_2$)$_p$CH=CR(CR$_2$)$_{\overline{q}}$R' where p, x and z are integers ranging from 1 to 20, inclusive, q is 0 or an integer ranging from 1 to 20, inclusive ; w is 0 or 1; R are alkyl groups, preferably having from 1 to 6 carbon atoms; R' is an alkyl group having from 5 to 20 carbon atoms; $R^F$ is a perfluoroalkyl group; Z is H or a F; and alkyl or alkoxy groups are those that have 5 to 20 carbon atoms.

36. The LC composition of claim 1 further comprising one or more compounds of formulas:

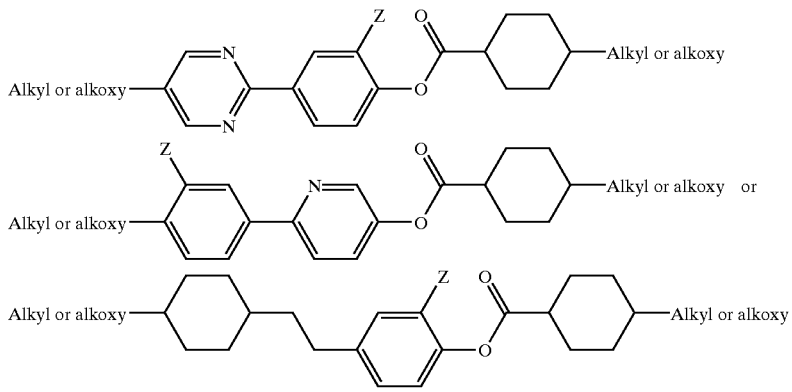

where Z is H or F.

37. A LC compound having the formula:

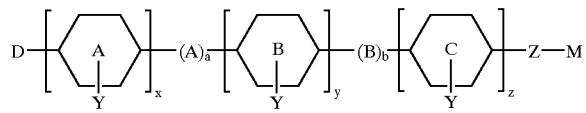

where D is:

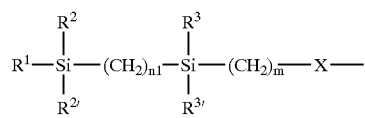

where:
R$^1$ is an alkyl or alkenyl group having j carbon atoms and R$^2$, R$^{2'}$, R$^3$ and R$^{3'}$, independently of one another, are alkyl groups having from 1–6 carbon atoms;
n1 and m are integers from 1 to about 20;
X is oxygen or a single bond; and
j is an integer from 1 to 18; and
wherein a, b, x, y, z can be 0 or 1; x+y+z is 1, 2 or 3, when x is 0, a is 0; when z is 0, b is 0;
A and B, independently, when present, can be —O—, —COO—, —OOC—, —CH$_2$—CH$_2$—, —CH=CH—, —C≡C—, —CH=CH—CH=CH—, —O—CH$_2$— or —CH$_2$—O;

the A, B and C rings, independently of one another, are aromatic rings or alicyclic rings, where one or two carbons in the A, B or C rings that are aromatic can be replaced with a N, O or S and one or two of the carbons in the A, B or C rings that are alicylic can be replaced with a N, O or S or a C=O group; provided that the A, B or C rings are not a 3,4-difluorppyridine ring;

Y can represent up to four substituents on aromatic rings and up to 10 substituents on an alicyclic ring where Y can a halogen, CN group, NO$_2$, alkyl or alkoxy;

Z is a single bond, an —O— or a —COO— or —OOC— group, and

M is R$^F$, where R$^F$ is a straight-chain or branched alkyl or ether group which is fully or partially fluorinated and contains up to 20 carbon atoms.

38. The LC compound of claim 37 wherein n1 is 1.

39. The LC compound of claim 37 where R$^F$ is:

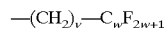

where v and w are integers ranging from 1 to 20, inclusive, and v+w is 5 to 20, inclusive.

40. An optical device which comprises an aligned layer of an LC composition of claim 1.

41. The device of claim 40 wherein the device is an SSFLC device.

* * * * *

UNITED STATES PATENT AND TRADEMARK OFFICE
CERTIFICATE OF CORRECTION

PATENT NO. : 6,783,812 B2
DATED : August 31, 2004
INVENTOR(S) : Wand et al.

It is certified that error appears in the above-identified patent and that said Letters Patent is hereby corrected as shown below:

Column 6,
Line 54, delete "prosperities" and replace with -- properties --.

Column 7,
Line 57, delete "Attorney Docket Nos. 106-00P and 86-00P" and replace with -- 60/255,984 and 60/256,229 --.
Lines 60-61, delete "regular applications Attorney Docket Nos. 106-00 and 86-00" and replace with -- Patent Nos. 6,759,101 and 6,737,124 --.

Column 8,
Line 58, delete "without" and replace with -- without --.

Column 10,
Lines 2, 40, 48 and 50, delete "R1'" and replace with -- $R^{1'}$ --.

Column 11,
Lines 6, 10 and 14, delete "R1'" and replace with -- $R^{1'}$ --.
Line 52, delete "to" and replace with -- two --.

Column 13,
Line 9, delete "are" after "typically".

Column 14,
Lines 37-38, delete "Attorney Docket Nos. 106-00P and 86-00P" and replace with -- Serial Nos. 60/255,984 and 60/256,229 --.
Line 44, delete "Attorney Docket No. 106-00P" and replace with -- U.S. provisional application 60/255,984 --.
Line 46, delete "Attorney Docket No. 86-00P" and replace with -- U.S. provisional application 60/256,299 --.
Lines 47 and 48, delete "Attorney Docket No. 106-00P" and replace with -- U.S. provisional application 60/255,984 --.
Line 49, delete "Attorney Docket No. 86-00P" and replace with -- U.S. provisional application 60/256,299 --.

Column 16,
Line 67, delete "Attorney Docket No. 75-99" and replace with -- serial no. 60/259,451 --.

Column 21,
Lines 20 and 55, delete "relux" and replace with -- reflux --.

UNITED STATES PATENT AND TRADEMARK OFFICE
CERTIFICATE OF CORRECTION

PATENT NO.     : 6,783,812 B2
DATED          : August 31, 2004
INVENTOR(S)    : Wand et al.

It is certified that error appears in the above-identified patent and that said Letters Patent is hereby corrected as shown below:

Column 21,
Lines 20 and 55, delete "relux" and replace with -- reflux --.

Column 24,
Lines 29 and 50, delete "roved" and replace with -- removed --.
Line 64, delete "$OC_8H_{16}Si(CH_3)_2CH_2Si(CH_3)$." from the structure and replace with -- $OC_8H_{16}Si(CH_3)_2CH_2Si(CH_3)_3$ --.

Column 25,
Lines 8, 35 and 67, delete "treaction" and replace with -- reaction --.

Column 26,
Lines 29 and 61, delete "treaction" and replace with -- reaction --.

Column 27,
Lines 26 and 61, delete "treaction" and replace with -- reaction --.

Column 28,
Lines 27 and 61, delete "treaction" and replace with -- reaction --.

Column 29,
Lines 27 and 61, delete "treaction" and replace with -- reaction --.

Column 30,
Between lines 45 and 50, delete "$OC_8H_{16}Si(CH_3)_2CH_2Si(CH_3)$." and replace with
-- $OC_8H_{16}Si(CH_3)_2CH_2Si(CH_3)_3$ --.
Lines 27 and 60, delete "treaction" and replace with -- reaction --.

Column 31,
Lines 26 and 60, delete "treaction" and replace with -- reaction --.
Between lines 45 and 50, delete "$OC_8H_{16}Si(CH_3)_2CH_2Si(CH_3)$." and replace with
-- $OC_8H_{16}Si(CH_3)_2CH_2Si(CH_3)_3$ --.

Column 32,
Lines 23 and 52, delete "treaction" and replace with -- reaction --.
Line 67, delete "Scheme 1".

UNITED STATES PATENT AND TRADEMARK OFFICE
CERTIFICATE OF CORRECTION

PATENT NO. : 6,783,812 B2
DATED : August 31, 2004
INVENTOR(S) : Wand et al.

It is certified that error appears in the above-identified patent and that said Letters Patent is hereby corrected as shown below:

Columns 57 and 58,
Table 2, in the Percent column, first entry, delete "4 00" and replace with
-- 4.00 --.
Table 2, in the Percent column, second entry, delete "8 00" and replace with
-- 8.00 --.

Columns 61 and 62,
Table 3, in the Percent column, first entry, delete "8 00" and replace with
-- 8.00 --.
Table 3, in the Percent column, second entry, delete "4 00" and replace with
-- 4.00 --.
Table 3, in the Percent column, third entry, delete "3 00" and replace with
-- 3.00 --.

Columns 63 and 64,
Table 4, in the Percent column, first entry, delete "3 00" and replace with
-- 3.00 --.
Table 4, in the Percent column, second entry, delete "1 00" and replace with
-- 1.00 --.

Columns 79 and 80,
Table 8, in the Percent column, first entry, delete "1 40" and replace with
-- 1.40 --.

Columns 85 and 86,
Table 10, in the Percent column, first entry, delete "3 06" and replace with
-- 3.06 --.
Table 10, in the Percent column, second entry, delete "1 02" and replace with
-- 1.02 --.

Column 90,
Line 54, delete "N;O" and replace with -- N,O --.
Line 56, delete "3,4-difluopropyridine" and replace with
-- 3,4-difluoropyridine --.
Line 59, delete "can a halogen," and replace with -- can be a halogen, --.

Column 92,
Line 7, delete "3,4-difluopropyridine" and replace with -- 3,4-difluoropyridine --.
Line 11, delete "can a halogen," and replace with -- can be a halogen, --.
Line 16, delete "or other group or $R^F$" and replace with -- or ether group or $R^F$, --
Line 35, delete "p, q, r, s, t, u, v, and w" and replace with -- p, q, r, s, t, and u --

UNITED STATES PATENT AND TRADEMARK OFFICE
CERTIFICATE OF CORRECTION

PATENT NO. : 6,783,812 B2
DATED : August 31, 2004
INVENTOR(S) : Wand et al.

It is certified that error appears in the above-identified patent and that said Letters Patent is hereby corrected as shown below:

Column 96,
Line 25, delete "3,4-difluopropyridine" and replace with
-- 3,4-difluoropyridine --.
Line 28, "can a halogen," and replace with -- can be a halogen, --.

Signed and Sealed this

Seventeenth Day of May, 2005

JON W. DUDAS
*Director of the United States Patent and Trademark Office*